US012213793B2

(12) United States Patent
Cohen

(10) Patent No.: US 12,213,793 B2
(45) Date of Patent: Feb. 4, 2025

(54) HEAD MOUNTABLE DEVICE

(71) Applicant: HeadSafeIP Pty Ltd, New South Wales (AU)

(72) Inventor: Adrian John Cohen, Sydney (AU)

(73) Assignee: HeadSafeIP Pty Ltd, New South Wales (AU)

( * ) Notice: Subject to any disclaimer, the term of this patent is extended or adjusted under 35 U.S.C. 154(b) by 0 days.

(21) Appl. No.: 18/365,653

(22) Filed: Aug. 4, 2023

(65) Prior Publication Data

US 2024/0023871 A1    Jan. 25, 2024

Related U.S. Application Data

(63) Continuation of application No. 16/610,444, filed as application No. PCT/AU2018/050402 on May 2, 2018, now abandoned.

(30) Foreign Application Priority Data

May 2, 2017    (AU) ................. 2017901590

(51) Int. Cl.
A61B 5/378    (2021.01)
A61B 5/00    (2006.01)
A61B 5/377    (2021.01)

(52) U.S. Cl.
CPC ............ *A61B 5/378* (2021.01); *A61B 5/0006* (2013.01); *A61B 5/377* (2021.01); *A61B 5/4064* (2013.01);
(Continued)

(58) Field of Classification Search
CPC ....... A61B 5/378; A61B 5/377; A61B 5/0006; A61B 5/4064; A61B 5/6803;
(Continued)

(56) References Cited

U.S. PATENT DOCUMENTS 5,331,969 A    7/1994    Silberstein
6,385,486 B1    5/2002    John et al.
(Continued)

FOREIGN PATENT DOCUMENTS

CN    104323785 A    2/2015
DE    3685657    7/1992
(Continued)

OTHER PUBLICATIONS

Communication under Rule 71(3) EPC Intention to Grant issued for European Application No. 18794787.4, mailed on May 23, 2023, 85 pages.
(Continued)

*Primary Examiner* — Patrick Fernandes

(57) ABSTRACT

A head mountable device for detecting a functional disorder of a brain in a patient, includes: an opaque visor unit for positioning over eyes of the patient, a plurality of reference sensors adapted to detect a reference electrical potential for the patient during exposure to the visual stimulus, and a sensor housing including at least one electroencephalogram (EEG) electrode for measuring electrical potential generated by the brain of the patient. The visor unit includes an arrangement of a plurality of LEDs positioned on an inside surface of said visor unit to which, during use, the eyes of the patient are exposed, and an LED driver, said LED driver being configured to control each of said LEDs independently to display a visual stimulus.

19 Claims, 25 Drawing Sheets

(52) U.S. Cl.
CPC .......... *A61B 5/6803* (2013.01); *A61B 5/7235* (2013.01); *A61B 2503/10* (2013.01)

(58) Field of Classification Search
CPC ... A61B 5/7235; A61B 2503/10; A61B 5/372; A61B 5/6814; A61B 5/369; A61B 5/37; A61B 5/371; A61B 5/373; A61B 5/374; A61B 5/375; A61B 5/376; A61B 5/0004
See application file for complete search history.

(56) References Cited

U.S. PATENT DOCUMENTS

| | | |
|---|---|---|
| 7,862,516 B1 | 1/2011 | Anschel |
| 2004/0082862 A1 | 4/2004 | Chance |
| 2005/0277826 A1 | 12/2005 | Dunseath |
| 2007/0249952 A1 | 10/2007 | Rubin et al. |
| 2011/0257489 A1 | 10/2011 | Banet et al. |
| 2014/0171820 A1 | 6/2014 | Causevic |
| 2014/0316221 A1 | 10/2014 | Rothman |
| 2014/0323899 A1 | 10/2014 | Silberstein |
| 2015/0374971 A1 | 12/2015 | Dar et al. |
| 2016/0007921 A1 | 1/2016 | Galea et al. |
| 2016/0192858 A1 | 7/2016 | Min |
| 2017/0035317 A1 | 2/2017 | Jung et al. |

FOREIGN PATENT DOCUMENTS

| | | |
|---|---|---|
| DE | 3685657 T2 | 12/1992 |
| WO | 2015055156 A1 | 4/2015 |
| WO | 2015161300 A1 | 10/2015 |
| WO | 2016182974 A1 | 11/2016 |

OTHER PUBLICATIONS

International Search Report and Written Opinion of the International Searching Authority for International Application No. PCT/AU2018/050402, mailed Jun. 8, 2018. 11 pages.

First Office Action and Search Report for Chinese Application No. 201880029482.X, mailed on Mar. 17, 2022 with English translation, 26 pages.

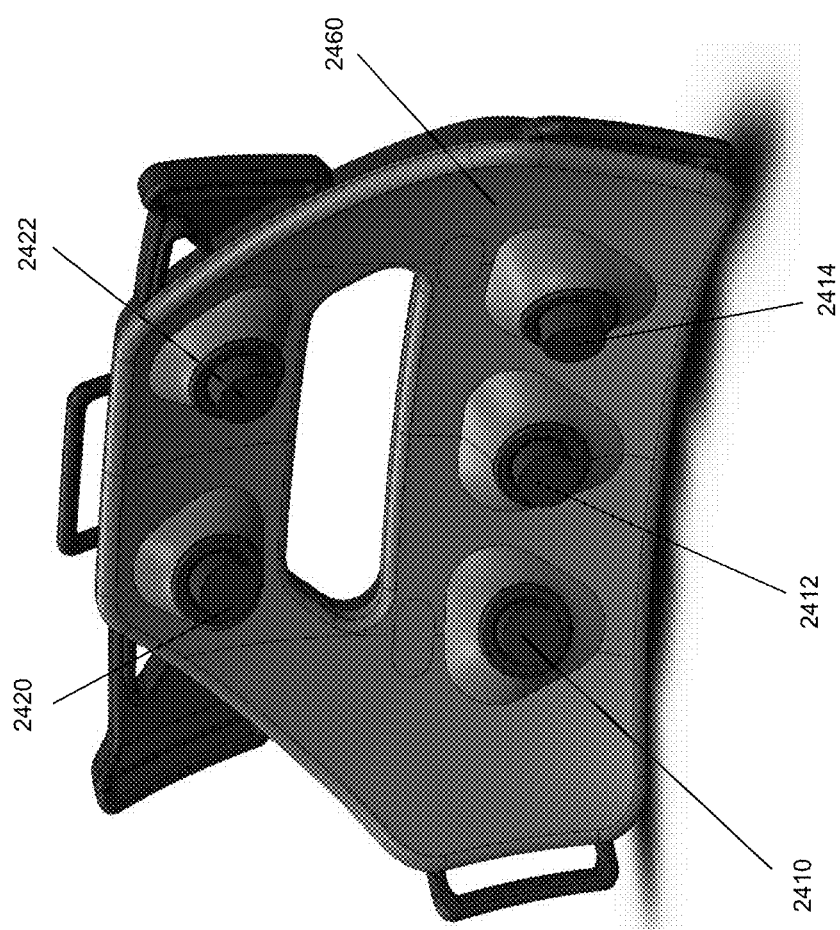

HEAD MOUNTABLE DEVICE

CROSS REFERENCE TO RELATED APPLICATION

This application is a continuation application of U.S. application Ser. No. 16/610,444 filed on Nov. 1, 2019, titled "HEAD MOUNTABLE DEVICE", which is a national phase application under 35 U.S.C. § 371 of International Application No. PCT/AU2018/050402, filed on May 2, 2018, which claims priority to Australian Patent Application No. 2017901590, filed on May 2, 2017, titled "HEAD MOUNTABLE DEVICE." The content of all of the above applications is hereby incorporated by reference in their entirety.

TECHNICAL FIELD

The present invention relates to an apparatus and method for detecting a functional disorder of the brain and, in particular, to detect a functional disorder of the brain by monitoring the electrical response of the brain to a visual stimulus.

BACKGROUND OF THE INVENTION

Mild Traumatic Brain Injury (mTBI) and other functional disorders of the brain can be the result of physical impact, in particular impact to the head. Observed symptoms of mild Traumatic Brain Injury include loss of memory, lack of orientation and delay brain processing speed. Such symptoms are typically recognised as concussion.

Mild Traumatic Brain Injury is often experienced in high impact sports, for example rugby, AFL and American football, as well as in other physical collisions, for example motor accidents. However, methods of diagnosis for mild Traumatic Brain Injury are typically subjective and often unreliable. For example it is difficult to detect mild Traumatic Brain Injury using MRI scans or CT scans.

Mild Traumatic Brain Injury is a dangerous condition. Patients suffering the condition require a prolonged recovery period. It is dangerous for an individual suffering mild Traumatic Brain Injury to receive a further impact before having recovered fully from the condition. This is particularly dangerous in a sports situation in which a decision needs to be made quickly as to whether a player should resume participation in the game following a collision. A reliable assessment of whether the player has sustained mild Traumatic Brain Injury is required in a limited time period.

One widely implemented test to assess mild Traumatic Brain Injury, particularly in sports, is the Sport Concussion Assessment Tool (fifth edition), SCAT5. SCAT5 is a standardised assessment for evaluating whether an athlete has sustained mild Traumatic Brain Injury. SCAT5 is widely used at all levels of sports to detect concussion and is endorsed by several sports governing bodies including FIFA, World Rugby and the International Olympic Committee. SCAT5 includes a series of functional, physical and neurocognitive tests performed on a potentially injured player. SCAT5 includes an assessment using several tests including the Glasgow Coma Scale (CGS) to assess consciousness, the Maddocks Score to assess the immediate memory of the player, as well as further physical, balance, coordination and cognitive tests to assess the player.

Although SCAT5 is widely recognised and implemented, many parts of the analysis are subjective. Consequently different physicians can conclude a different diagnosis on the same player. And players themselves are learning to provide answers to either downplay or alternatively exaggerate their symptoms. Metanalysis of sensitivity and specificity of the test This presents a problem to accurate diagnosis of the condition of the player. Overall, there is a possibility for errors and inaccuracies in diagnosis of mild Traumatic Brain Injury using subjective tests including SCAT5.

Embodiments of the present invention address some problems of the prior art by providing a new apparatus and technique for assessing functional performance of the brain.

SUMMARY OF THE INVENTION

In a first aspect, the present disclosure provides a head mountable device for detecting a functional disorder of the brain in a patient, comprising:
an LED display including a plurality of LEDs and an LED driver, said LED driver being configured to control each of said LEDs to display a visual stimulus;
at least one electrode for measuring electrical potential;
the device being configured to be mountable on the head of a patient such that when mounted on the head of a patient the LED display is positioned before the eyes of a patient and the at least one electrode is positioned adjacent to the occipital lobes of the patient.

In embodiments the LED display is configured to display a visual stimulus.

In embodiments the visual stimulus is a light pulse.

In embodiments the visual stimulus is white light.

In embodiments the visual stimulus pulses at a frequency of between 5 Hz to 60 Hz.

In embodiments the visual stimulus pulses at a frequency of 15 Hz.

In embodiments at least one electrode is configured to detect electrical signals from the occipital lobes of the patient in response to the visual stimulus when the device is mounted on the head of a patient.

Embodiments further comprise a processor configured to receive electric potential signal data from the at least one electrode.

Embodiments further comprise a memory, the memory being configured to store predetermined electrical potential values, wherein the processor is configured to compare received electric potential signal data with predetermined electric potential data to detect a functional disorder of the brain.

In embodiments the predetermined electric potential values are at least one of:
amplitude of the electric signal;
frequency of the electric signal; or,
latency of the electric signal.

In embodiments the functional disorder of the brain is concussion. In further embodiments the functional disorder is neurological impairment (acute or chronic) or other neurological disorders, for example dementia or MS.

Further embodiments comprise a wireless transmitter, the wireless transmitter configured to transmit the electric potential signal data to the processor over a radio communications network.

Further embodiments comprise a receiver, the receiver configured to receive activation signals for the LED display, the LED display being configured to display a visual stimulus on receipt of an activation signal.

In embodiments the receiver is a radio receiver configured to receive activation signals from a computing device across a wireless communications network. In embodiments the wireless communication network is WiFi, Bluetooth or another suitable wireless communication network.

In a second aspect, the present disclosure provides a method for detecting a functional disorder of the brain in a patient, the method comprising the steps of:

using a head mountable device including a plurality of LEDs and an LED driver, said LED driver being configured to control each of said LEDs, to provide a visual stimulus to the patient;

measuring an electrical response of the brain to the visual stimulus using at least one electrode positioned adjacent to the occipital lobe of the patient; and comparing the electrical response of the brain to predefined electrical data to detect a functional disorder of the brain.

In embodiments the visual stimulus is provided by an LED display and the electrical response of the brain is measured by at least one electrode; the device being configured to be mountable on the head of a patient such that when mounted on the head of a patient the LED display is positioned before the eyes of a patient and the at least one electrode is positioned adjacent to the occipital lobe of the patient.

In a third aspect, the present disclosure provides a system for detecting a functional disorder of the brain in a patient, the system comprising:

a head mountable device for detecting a functional disorder of the brain in a patient, comprising:

an LED display including a plurality of LEDs and an LED driver, said LED driver being configured to control each of said LEDs to display a visual stimulus;

at least one electrode for measuring electrical potential;

the device being configured to be mountable on the head of a patient such that when mounted on the head of a patient the LED display is positioned before the eyes of a patient and the at least one electrode is positioned adjacent to the occipital lobe of the patient;

a receiver for receiving electric potential signal data from the at least one electrode; and a wireless transmitter for transmitting said received electric potential signal data; and a computing device, said computing device including:

a radio receiver for receiving said transmitted electric potential signal data;

a memory for storing predefined results; and a processor for comparing said electric potential signal data with said predefined results to diagnose a condition of the patient.

Embodiments of the present disclosure use electroencephalogram (EEG). By recording the brain's electrical activity at the level of the scalp, neuronal activity can be objectively analysed. EEG testing is low-risk and relatively low cost, making it ideal for widespread use.

Event-related potentials (ERPs) are a subset of EEG which evaluate the brain's response to stimuli rather than examining passive activity.

Embodiments use visual evoked potentials (VEPs), a type of ERP, recorded following pattern oscillation or flicker visual stimulus, to assess the integrity of the visual pathway from the cornea to the V1 visual cortex.

Embodiments compare the variance or a pattern of variance of the VEPs from baseline or normative models.

Embodiments of the present disclosure provide a device to challenge the brain that subtle as well as extreme reductions in mentation (neurological function), such as occur with concussion (mild traumatic brain injury), dementia and stroke for example, can be detected reliably and in a repeatable fashion. In embodiments, the means of the challenge relate to the nature of the stimuli put to the brain, the means of reliably presenting them and the effectiveness (sensitivity and specificity) of measuring the results.

These detectable changes might be acute, ie following recent trauma, or chronic, representing sub-clinical damage that is not able to be visualised on conventional imaging techniques (such as CT or MRI) or more advanced functional modalities including fMRI and DTI (diffusion tensor imaging) etc.

In addition, analogous to a hearing test where the response to various frequencies is detected and then can be longitudinally monitored, embodiments determine and record the response to various stimuli, both in isolation and in combination, to determine whether these differ from previous recordings in the same individual and to population norms. Embodiments of the device and its driving software can adapt subsequent testing for that patient to particularly explore those areas of difference looking for deterioration or recovery.

Applied stimuli may have a test routine to determine and modulate the effect is equal in each case to that desired.

As the stimuli in many cases will be faint, as will be the responses, the connectivity of the sensors to the brain is important. Typical passive (non-powered) EEG electrodes require a gel or saline solution to be applied intermittently.

BRIEF DESCRIPTION OF THE DRAWINGS

FIG. 25 shows a component of the third embodiment.

DETAILED DESCRIPTION OF THE DRAWINGS

Example 1

Figure 1:
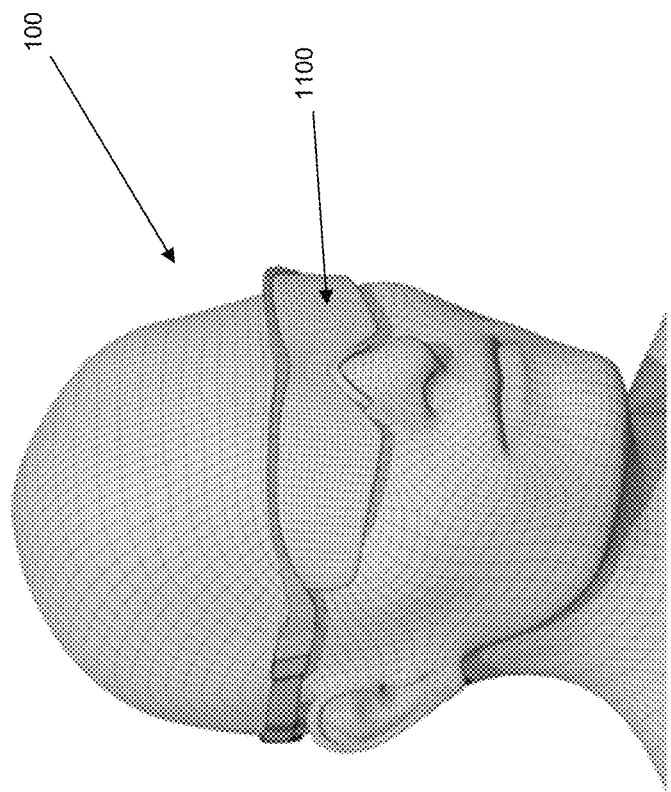
FIG. 1 shows a front view of an embodiment mounted on the head of a patient.
Figure 2:
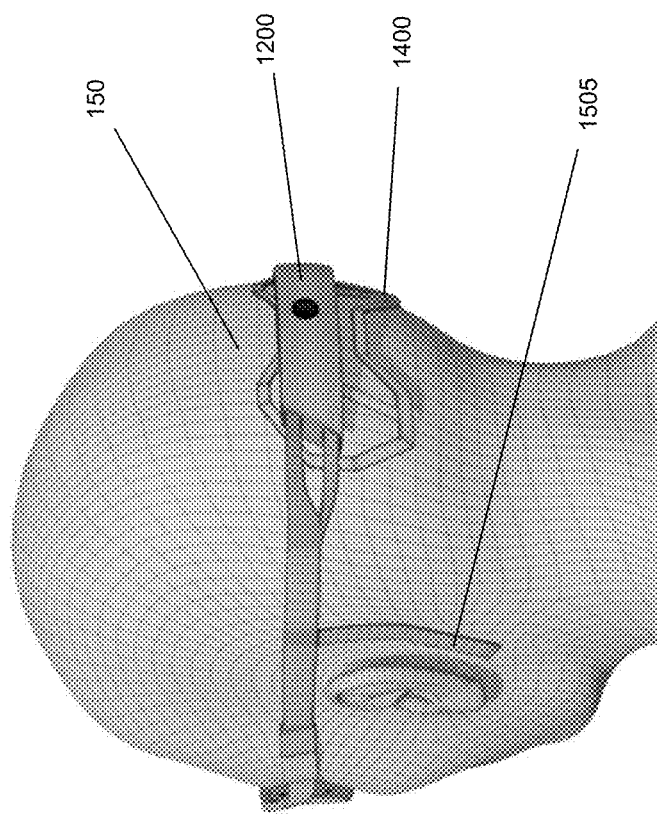
FIG. 2 shows a rear view of an embodiment mounted on the head of a patient.
Figure 3:
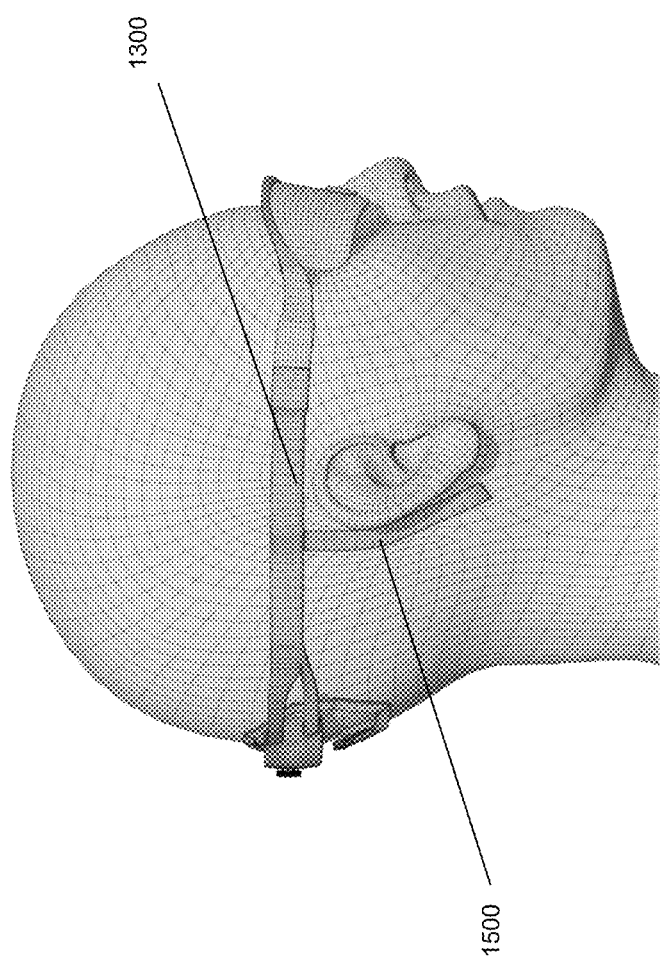
FIG. 3 shows a side view of an embodiment mounted on the head of a patient.

Referring now to the drawings there is shown a head mountable device for detecting a functional disorder of the brain in a patient. FIGS. 1 to 3 illustrate an embodiment of the device worn on the head of a patient. The device is configured to provide a visual stimulus to a patient and to measure the evoked potential from the visual response using a plurality of electrodes positioned adjacent and superficial to the skull overlying the occipital lobes of the patient. The occipital lobes are the parts of the brain largely responsible for visual processing.

Device 100 includes an opaque visor 1100 positioned over the eyes of the patient. The visor includes an arrangement of LEDs on the inside of the visor to which the patient's eyes are exposed (shown in FIG. 5). The LEDs are arranged to provide a visual stimulus to the patient when the device is activated. The device 100 includes a housing 1200 arranged to be positioned at the back of the patient's head. Housing 1200 includes at least one electrode for measuring electrical potentials generated by the brain of the patient. Electrodes are positioned within housing 1200. The device is configured such that housing 1200 is located superficial to the skull overlying the region of the occipital lobes 150 of the patient's head. Device 100 includes headband 1300 and support portion 1400 to maintain the position of device 100 on the patient's head.

Arms 1500 and 1505 extend from headband 1300 and are configured to be positioned behind the ears of a patient. Each arm 1500 to 1505 includes a reference electrode. Reference electrodes are activated to detect a reference electrical potential for the patient during exposure to a visual stimulus.

During activation of the visual stimulus the electrodes measure electrical potential. The device uses the measured electrical potential to detect a functional disorder of the brain as discussed in more detail below.

Figure 4:
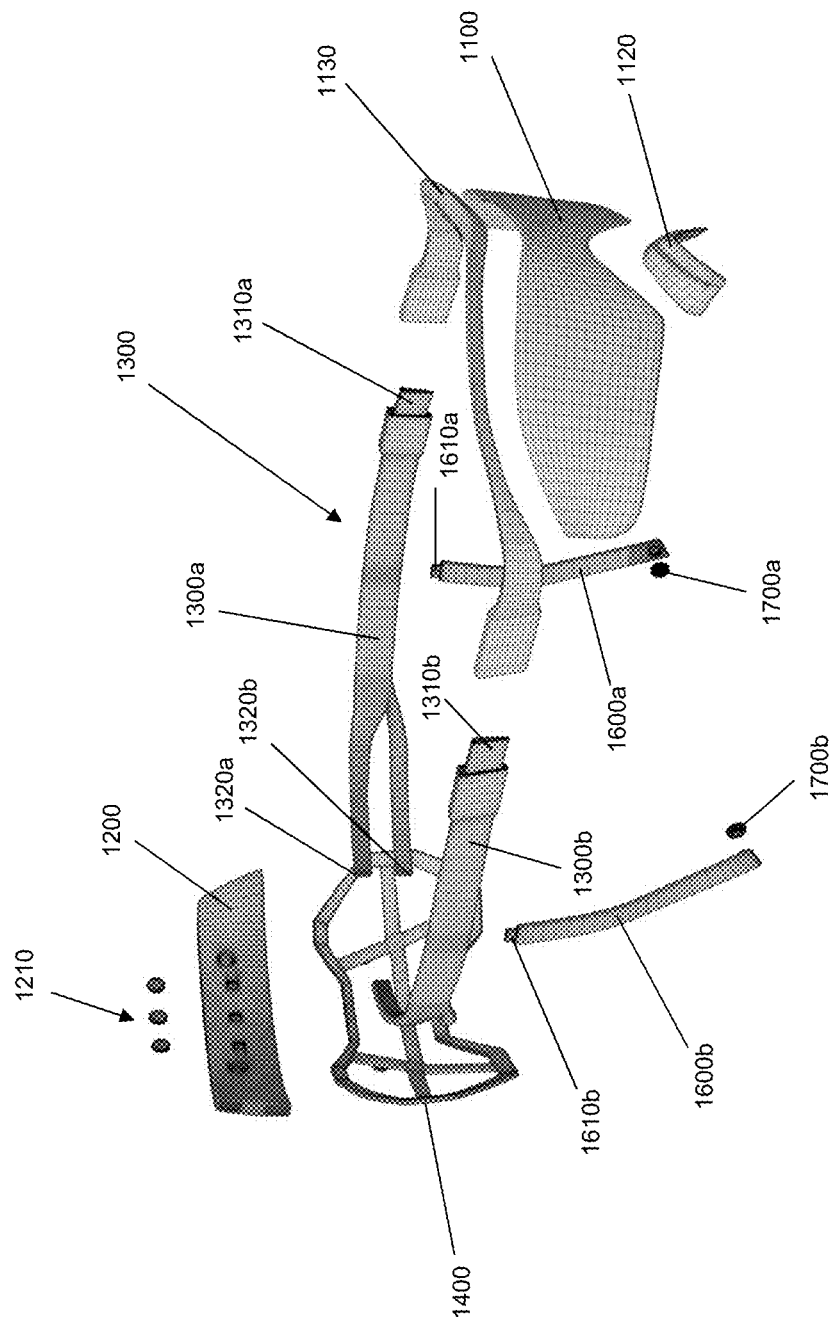
FIG. 4 shows an exploded view of an embodiment.
Figure 5:
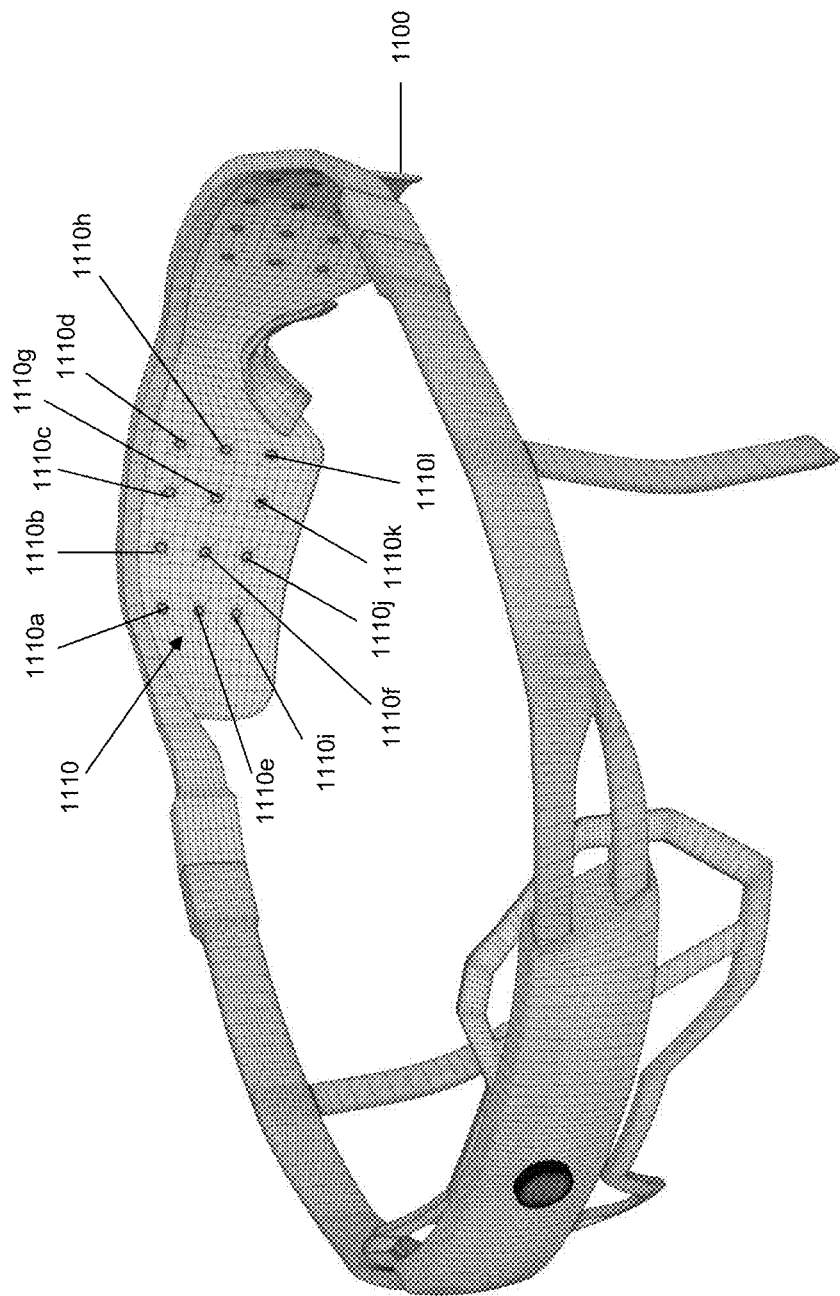
FIG. 5 shows a rear view of an embodiment.
Figure 6:
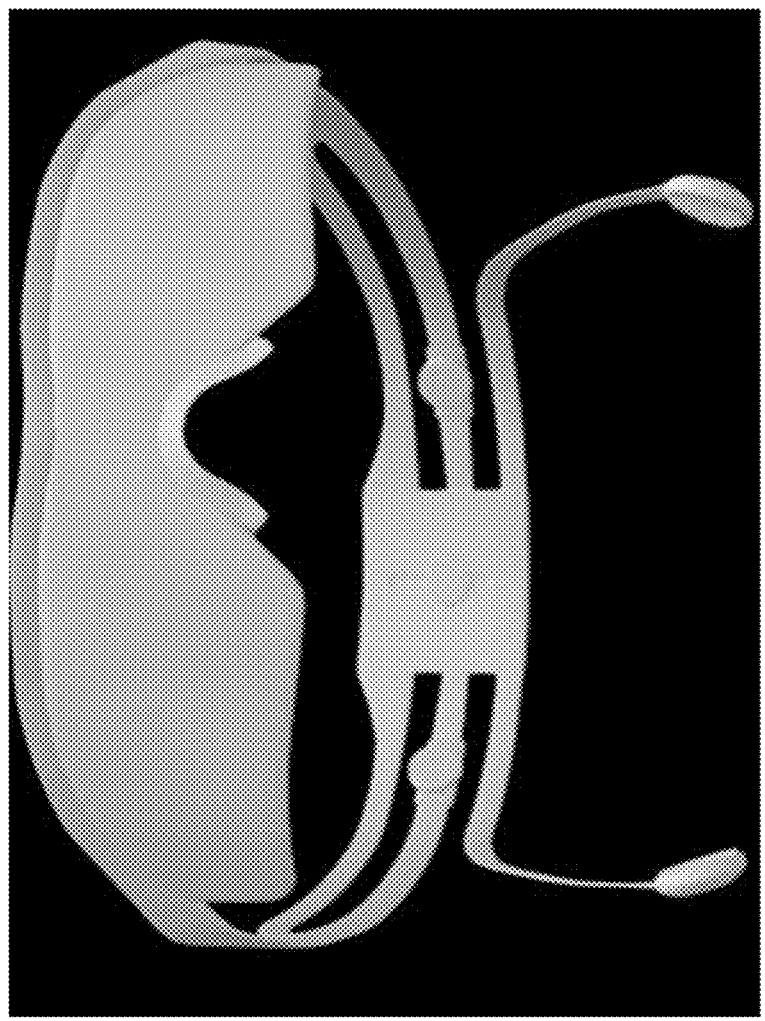
FIG. 6 shows an underside view of an embodiment.

Device 100 is described in more detail with reference to FIGS. 4-6. FIG. 4 shows an exploded view of device 100. Visor 1100 is opaque and constructed from a polymer material. Visor 1100 is attached to bridge 1120 to position visor 1100 on a patient's nose. Top bar 1130 is attached to visor 1100 to connect visor 1100 to headband 1300.

A further embodiment of the head mountable device is shown in FIGS. 18-21.

The embodiment of FIGS. 18-21 has a different construction to that of the device of FIGS. 1-3 but includes equivalent components. Visor 1810 (shown in exploded view in FIG. 19) is arranged to be positioned over the eyes of a patient when device 1800 is positioned on the patient's head. Sensor housing 1840 is positioned at the rear of the patient's head. Sensor housing 1840 includes EEG sensors 1852, 1854, 1856 configured to be positioned over the occipital lobes when the device is mounted on a patient's head. The device 1800 is held in position on the patient's head by headband 1820, 1825. Additional support is provided by top headband 1830. Headbands 1820, 1825, 1830 include adjustors 1822, 1824, 1834 respectively to allow the device to be tightly fitted to a patient's head.

Visor unit 1810 includes opaque visor 1812. Headband fitting 1418 is positioned inside opaque visor 1812 and includes a top extending portion 1813 extending from the visor to provide an anchor point for top headband 1830. Reference electrode 1815 is positioned within portion 1813. Reference electrode 1815 provides a reference signal for use in analysis of patient data. Notice that in the embodiment of FIGS. 18-21 reference electrode is positioned around the forehead of the patient. This is in contrast to the embodiment of FIGS. 1-6 in which reference electrodes are positioned behind the ears of a patient. Visor 1810 includes LED source 1818 to provide the visual stimulus to a user. A skin interface gasket 1819 is positioned to contact the face of the patient when the device is mounted on the head.

Figure 20:
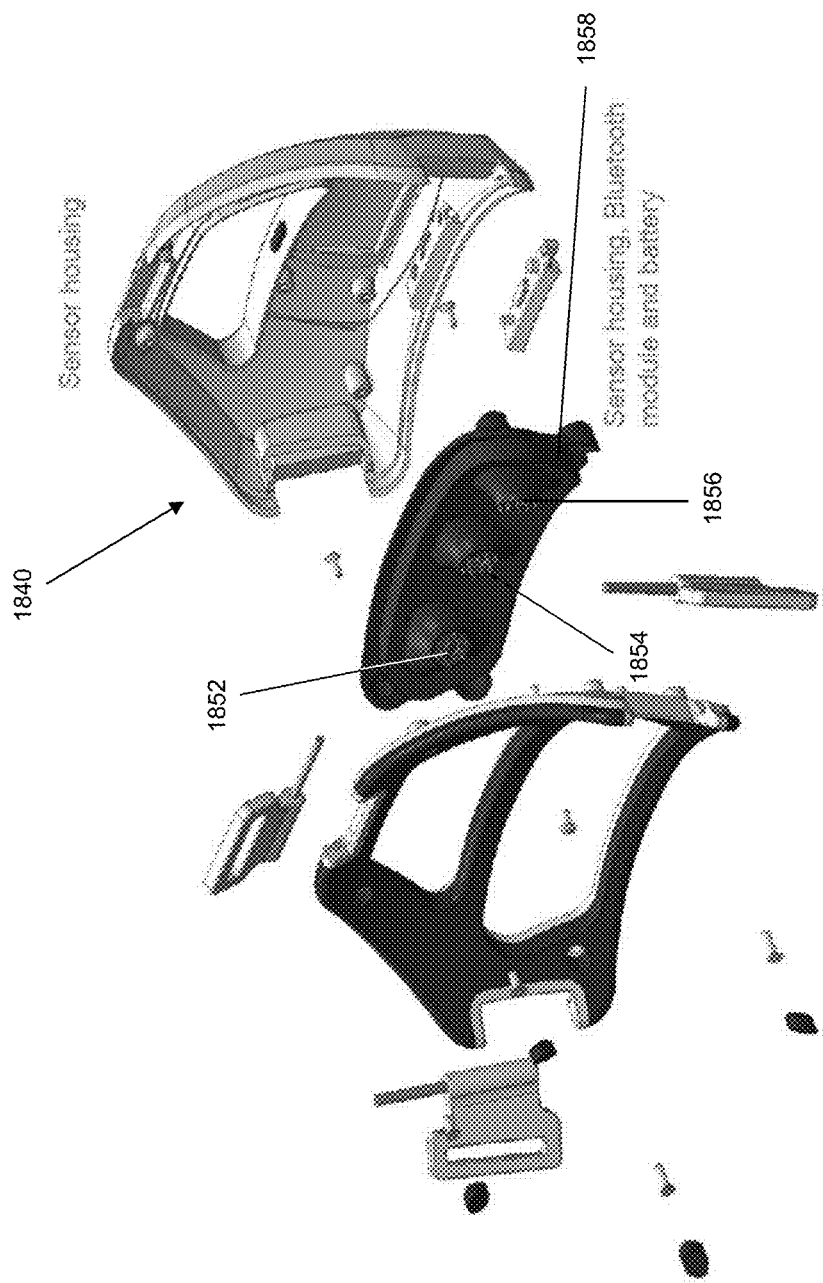
FIG. 20 is an exploded view of the sensor housing in the second embodiment.
Figure 21:
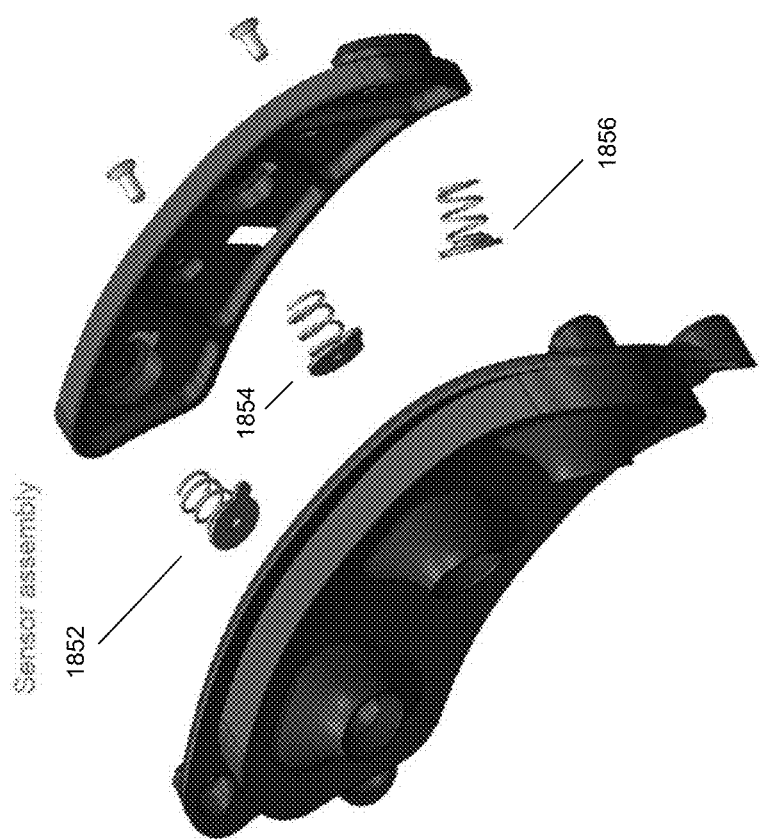
FIG. 21 is an exploded view of sensor plates in the second embodiment.

The sensor housing 1840 is shown in exploded view in FIGS. 20 and 21. Sensor housing includes sensors 5218, 5418, 1856 mounted on sensor plates 1858. Sensor plate 1858 is shown in exploded view in FIG. 21 with sensors 1852, 1854, 1856 positioned within the sensor plate. Bluetooth module and battery are also positioned within sensor housing 1840.

Figure 24:
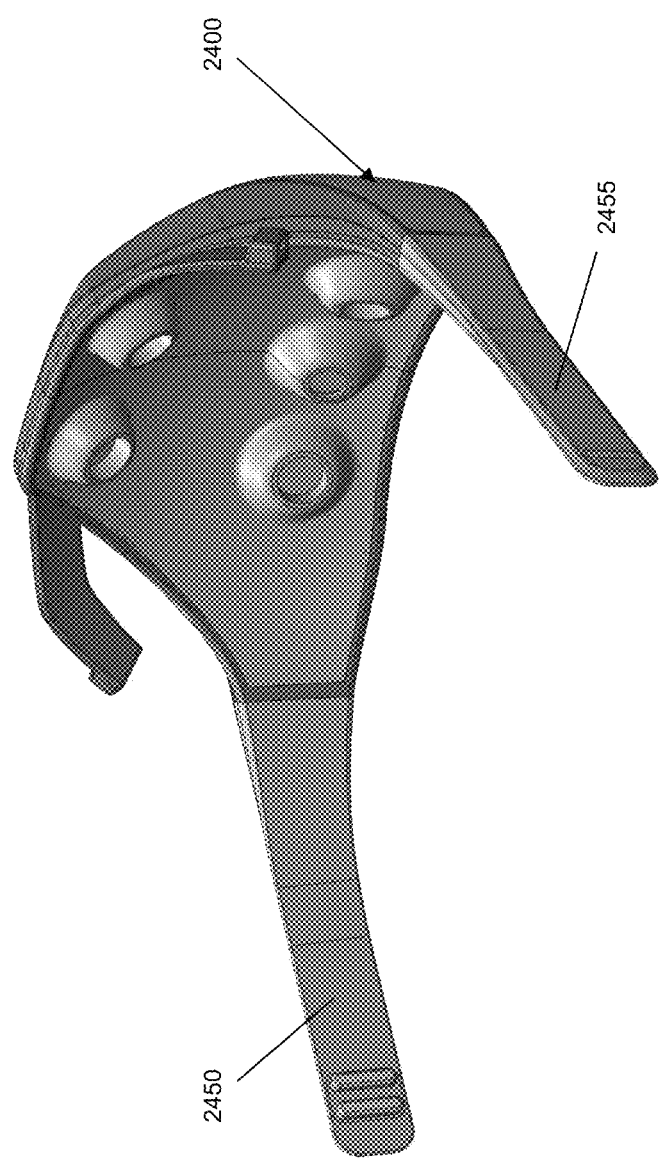
FIG. 24 is a perspective view of a third embodiment.

A further embodiment of the head mountable device is shown in FIGS. 24 and 25. These Figures only show the rear portion of the device, without any visor or visual stimulus screen.

In the embodiment of FIGS. 24 and 25, three EEG sensors 2410, 2412, 2414 are mounted on sensor plate 2460. Two reference sensors 2420, 2422 are located above the EEG sensors on the sensor plate 460 Sensor plate is contained within sensor housing 2400.

Sensor housing is configured to be positioned on the head of a patient at the rear of the patient's head in order that the EEG sensors are positioned over the occipital lobes when the device is correctly positioned on the head of the patient.

The device has arms 2450, 2455 to support the device on the head of the patient. These arms may be connected to visor.

LED Arrangement

An arrangement of LEDs 1110 is positioned on the inside of visor 1100. In the example of FIG. 5, LEDs 1110 are positioned in a rectangular configuration on each side of visor 1100, with LEDs 1100 including LEDs 1110a . . . 11101 positioned on an inner left side of the visor 1100 and a corresponding number of the LEDs 1100 positioned on an inner right side of the visor 1100. The arrangement includes rows of four LEDs running horizontally across the inside surface of visor 1100 and three rows of LEDs running vertically down inside the face of the visor. LEDs are arranged in a uniform configuration having equal spacing between rows and columns. LEDs are positioned symmetrically on both sides of the bridge and provide a symmetrical arrangement before each eye of the patient. In the example of FIG. 5, LEDs 1110 emit white light.

LEDs 1110 are powered by a battery positioned within housing 1200. Electrical power is provided to LEDs 1110 via electrical conductors positioned within headband 1300, top bar 1130 and into visor 1110.

Housing 1200 also includes an LED driver. LED driver controls activation of each LED within LED arrangement 1110. LED driver controls each LED independently.

Consequently different illumination sequences can be created including simultaneous illumination of LEDs, sequential illumination of LEDs and selective activation of LEDs. LED driver is programmable to implement multiple different LED illumination sequences. The flashing frequency or variation of flashing frequency is controlled by LED driver.

LED driver can provide activation and deactivation of LEDs at specific frequencies. Typical illumination frequencies for LEDs 1110 are between 5 Hz to 60 Hz. Preferred embodiments illuminate LEDs 1110 at operational frequency of 15 Hz.

This frequency range is desirable as the strongest visual response from the brain lies from 10-15 Hz, and for higher frequency responses, 40-60 Hz.

In some embodiments, intermittent lighting sequences are used including periodic bursts of lighting (stimulation periods) and breaks. The stimulation periods may be regular or irregular. Typical breaks between stimulation periods may be 0.1 to 100 seconds. For example a first 30 second stimulation burst may be followed by a 10 second break, followed by a further 30 second stimulation period, followed by a further 10 second break, followed by a further stimulation period. The duration of the stimulation periods and breaks may be varied and the light sequences may be varied depending on the operating parameters for the system. The durations of the stimulation periods and breaks can be optimally set at intervals that may produce more pronounced results.

The stimulation may include sectoral variability of applied stimulus for the visual field, for example different eyes may be isolated. This may include left/right alternation, variance and sequencing with the ability to isolate each eye and each visual field.

The time period pattern for stimulation may be varied in a sequence of progressively lengthening or randomly varying time periods to provide unique corresponding electric potential signals to distinguish latency and avoid potential artefacts arising from conditioning.

In some embodiments the LED driver automatically sweeps through a series of frequencies and variations in periods of stimulation or non-stimulation.

In some embodiments the LEDs are driven simultaneously to create the visual stimulus. Alternative flashing arrangements may also be used in which LEDs are activated in an alternating flashing sequence or a sweeping left-to-right (or right-to-left, top-to-bottom, bottom-to-top) flashing pattern. Additional lighting sequences are used in further embodiments.

Further embodiments include an LED shutter system that transmits or blocks ambient light to a controlled frequency by controlling 'opaqueness (from no transmissibility to close to full transmissibility) in the headset lenses instead of generating its own light. Typically the shutters are positioned in the glasses or visor. The shutter system may have a separate driver controlled by the processor or it may be controlled by the LED driver.

Some embodiments use additional operational frequencies beyond the 5-60 Hz range.

Preferred embodiments include white LEDs. White LED's may be constructed from a series of three smaller red, green and blue LED's which, when combined, display a white colour. Alternatively, a blue LED in combination with yellow phosphor may also be used to generate a white LED. Different wavelengths or variations in wavelengths may be used.

In addition to white LED's, addressable LED's may also be used to vary the colour output to acquire potentially different results.

Embodiments may utilise any range of preferred safe visible light frequencies ranging from near infra-red to blue light.

Brightness and intensity of the LED's may be adjusted manually from the software as part of the initial setup. A hardware control is also to be used to control the LED's brightness and colour output.

In further embodiments, alternative light sources to LEDs are included. Further embodiments include combinations of LEDs with alternative light sources.

Further embodiments of the invention include different arrangements of light sources.

In further examples of the visor, the screen may be physically patterned, for example corrugated, for Visually Evoked Stimuli. Some embodiments of the visor include EMG on the screen to detect a physical response to the light sequence, including blink response and aversion.

Further embodiments include polarised light elements.

Simultaneous different light patterns may be applied during the test sequence. Measurement of the EEG response allows detection of suppression of one or more of the applied stimuli.

Electrodes

Housing 1200 includes three active electrodes 1210. Electrodes are configured to measure electrical potentials of up to 100 pV.

A variety of electrodes may be employed in the system. The example of FIG. 4 includes active electrodes which contain circuitry located a very short distance away from the electrode. This circuitry, which is comprised of a pre-amplifier, allows the electrodes to have very high input impedance, allowing use with dry skin.

Electrodes 1210 are connected to a processor positioned within housing 1200. Processor controls activation and deactivation of electrodes 1210.

In further embodiments the number of electrodes and the specific position of the electrodes may be varied.

Headband Configuration

Headband 1300 is configured to join housing 1200 to visor 1110. In the embodiment of FIGS. 3-6 headband 1300 is constructed in two pieces 1300a and 1300b on either side of the device. Headband is constructed from polymer material and is sufficiently flexible to allow comfortable and accurate positioning of the device on the patient's head. Headband may also include length adjustors to facilitate accurate positioning of the device on heads having different circumferences. Headband 1300 includes electrical wires to carry electrical input signals from housing 1200 to visor 1110.

Headband 1300 includes plugs 1310a, 1310b for connection to top bar 1130. Plugs 1310a, 1310b provides electrical connection between housing 1200 and visor 1100. Plugs 1310a, 1310b also provide physical connection to top bar 1130.

At the rear of the device headband 1300 connects to housing 1200. Each side of headband 1300 includes two connection points 1320a, 1320b to housing 1200. Connection points provide electrical and physical connection between headband 1300 and housing 1200.

Support 1400 is positioned at the rear of the device. Support 1400 is made from polymer and configured to hold the device in position on the head of the patient. In particular, the shape of the support section 1400 is rounded to hold the housing 1200 in close proximity to the occipital lobes at the back of the head.

Device 100 includes two arms 1600a 1600b extending from headband 1300. Arms 1600a 1600b are positioned behind the ears of the patient when being correctly worn. Arms 1600a 1600b extend from headband 1300. A reference electrode 1700a, 1700b is positioned at a distal end of each arm. Reference electrodes 1700a 1700b are active electrodes. Arms 1600a, 1600b include electrical wiring to carry activation signals to reference electrodes 1700a 1700b and to transmit recorded signals from the electrodes to housing

1200. Each of arms 1600a, 1600b includes connector 1610a 1610b configured to provide electrical connection and physical connection to headband 1300.

In further embodiments the reference electrodes may be positioned at other locations around the patient, for example in housing 1200.

The positioning of the headset on a patient is illustrated in FIGS. 1-3 when positioned on the head of a patient visor 1100 is arranged to position LEDs directly in front of the eyes of the patient. The visor is arranged to provide full visual coverage to prevent visibility outside the LED array. Support section 1400 is rounded to engage the back of the patient's head and to maintain the position of housing 1200 in close proximity to the occipital lobes of the patient's brain. Arms 1500 are positioned behind patient's ears and the reference electrodes are located in the region of the patient's ear lobes. Embodiments of the invention facilitate adjustable sizing of the headband in order that the device can be worn by individuals having different head circumferences.

The positioning of the electrodes on the head can be controlled by circuitry detecting electrode impedance to detect positioning and the adequacy of the contact to the head. The contact detectors detect contact with the head and the position of the electrode on the head of the patient. For each patient a contact memory is created, this contact memory may be a data file stored with the patient's record to record the position of the electrodes. This allows electrode placement to be replicated and allows the device to be positioned quickly and accurately on the patient's head.

Operation and Control of the Headset

Figure 7:
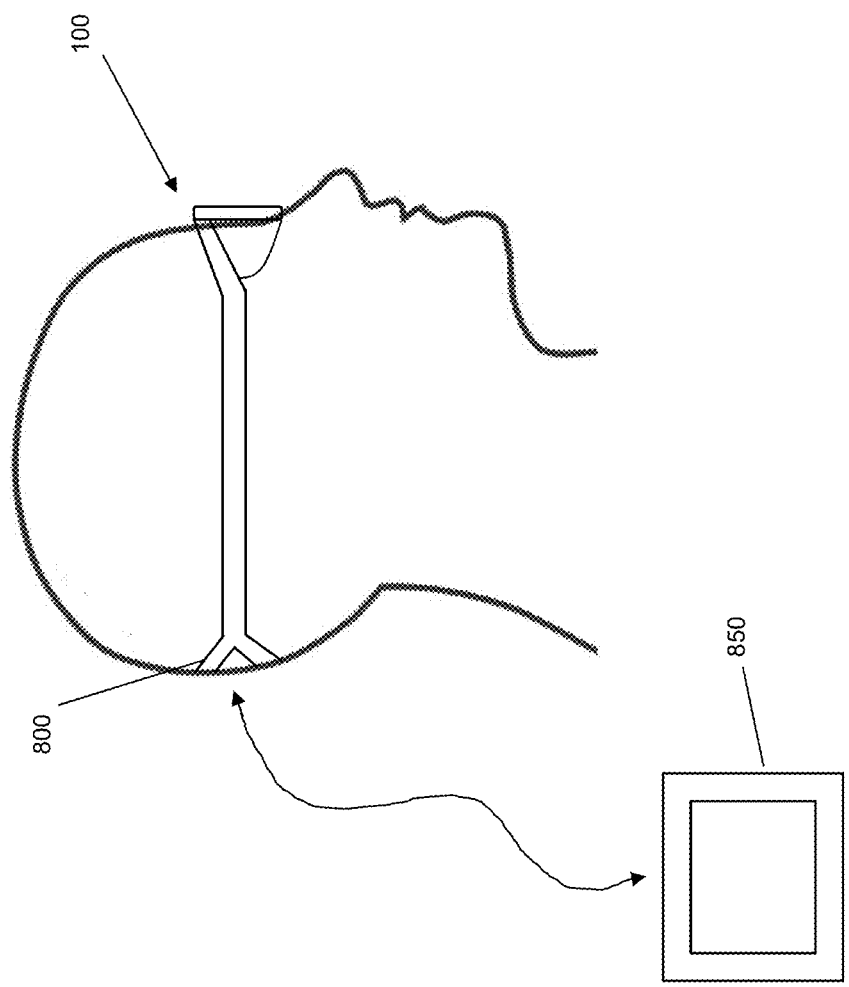
FIG. 7 shows a system including a headpiece and a computer processing unit.
Figure 8:
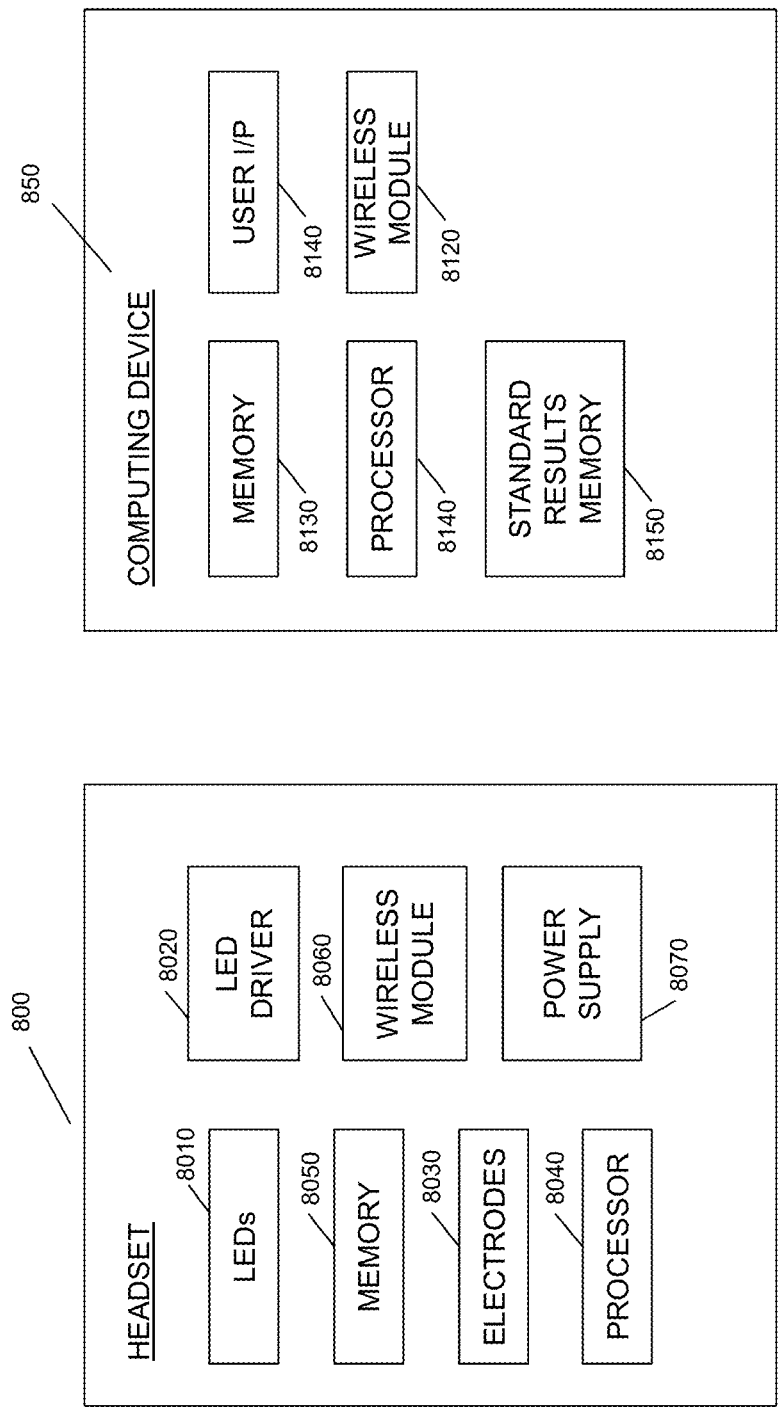
FIG. 8 is a block diagram showing components in an embodiment.

The operational components of the headset and control device are illustrated in FIGS. 7 and 8. As discussed previously, headset 800 includes LEDs 8010 activated by LED driver 8020 positioned in housing 1200. The LEDs 8010 are connected to the LED driver via a series of electrical connections running through the headband between housing 1200 and visor 1100. As discussed above, electrodes 8030 are located in housing 1200 and configured to be in the proximity of the occipital lobes of the brain of the patient when the device is fitted to the head of a patient. Reference electrodes are also positioned on the headset, these may be positioned in various positions around the head depending on the configuration of the headset, for example behind the patient ears (for examples FIGS. 1 to 3), above the sensor electrodes (see for example FIGS. 24 to 26) or towards the front of the head (see for example FIGS. 18 and 19).

Further embodiments may include combinations of positions for reference electrodes.

Electrical control of the headset is provided by processor 8040. In preferred embodiments of the invention processor 8040 is positioned in housing 1200. However, it will be clear that processor 8040 could be positioned at any location within the headset unit. Processor 8040 provides activation information to LED driver 8020 which subsequently controls activation of LEDs 8010. Processor 8040 also controls activation and deactivation of electrodes 8030. Electrodes 8030 are connected to memory 8050. Memory 8050 receives the measured electric potentials from each electrode, stores and transmits the values for analysis.

Preferably, during a test, memory 8050 stores all information relating to the activation sequence of the electrodes. Memory 8050 also stores the measured potential values from each electrode in response to the activation sequence. Further information relating to the test, for example information regarding the location of the test, duration of the test, and the date and time of the test may also be recorded in memory 8050. The purpose of memory 8050 is to store data associated with the test. Preferred embodiments of the invention include a memory module within headset 100 but further embodiments may include a remotely positioned memory connected the headset. The connection may be via a wired connection or via a wireless connection. Headset 800 also includes power supply 8070 for providing power to the electrical components of the device.

Preferred embodiments to the invention provide wireless control of the headset from a computing device across a wireless communications network. Suitable wireless communications networks include WIFI, Bluetooth, mobile communication networks, or other suitable wireless communication networks. In such embodiments a wireless module 8060 is incorporated into headset 800. Wireless module 8060 includes a radio receiver to receive control information for headset 800 and a wireless transmitter to transmit performance data from headset 800 to a controlling computer device.

FIG. 7 illustrates the connection between control device 850 and headset 800. Control device 850 includes wireless module 8120 including a radio receiver to receive performance data from headset 800 and a wireless transmitter to transmit control signals to headset 800. Control device 850 includes user input device 8110. User input device is configured to receive user input to control the computing device and consequently headset 8110. User input device may be a keyboard, touch screen, microphone or other suitable device to receive a user instruction.

Computing device 850 includes memory 8130. Memory 8130 includes standard operating parameters for the headset and also stores performance results for headset 800. Memory 8130 may include different operating sequences for headset 800 associated with different tests for a patient. Further embodiments of the invention store comparative results within a memory of the computing device 8150. This may be within the same memory 8130 or within a separate memory unit. The comparative results are stored in order that headset can compare measured electrical potential from the electrodes with predefined results to diagnose a condition of the patient. Computing device is controlled using processor 8140.

As discussed above, interaction between computing device 850 and headset 800 is provided across a wireless communication network. In further embodiments communication may be provided between headset 800 and computing device 850 using a wired connection, for example a USB or other electrical or optical connector capable of exchanging data between the devices.

In embodiments of the invention computing device 850 is a mobile telephone. An application may be loaded onto the computing device to enable interaction with headset 800. Alternatively, a designated computing device may be paired to headset 800. Any computing device with suitable connectivity components and control components could be used to control the headset and to interact with the headset.

Embodiments of the invention can be connected to the internet ("cloud based storage systems" and "cloud based processing systems"). Such systems include communication modules in the headset and/or in the computing device to transmit and receive data across the internet or other data networks. Patient data and test data can be transmitted and received across these networks to enable remote storage and analysis of patient data. Data can also be retrieved for local analysis. In an example, the capability of sharing processor and diagnostic data from single and multiple systems with a software and dashboard interface can facilitate review and analysis by a concussion specialist, team coach or safety officer. The dashboard may provide real-time data as well as historical summaries for individual users, groups and populations.

Operation Procedure

Figure 9:
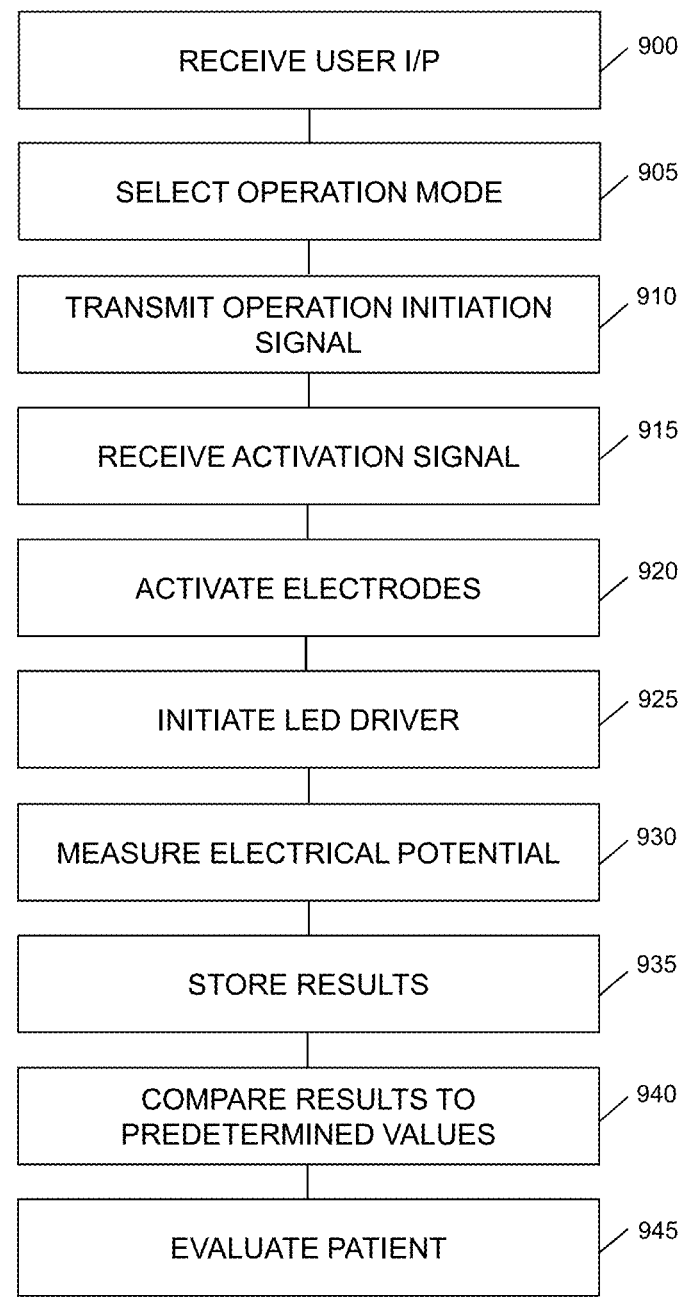
FIG. 9 is a flow diagram showing steps performed by an embodiment.

FIG. 9 is a flow chart showing the steps taken during operation of an embodiment of the headset.

At 900 computing device 850 receives user input. Computing device 850 is configured to receive user input requesting the headset to undergo a test routine. In preferred embodiments the computing device includes at least one preconfigured routine including specific parameters for the test. Parameters may include duration of the test, sequence of LED operation, for example the frequency which LEDs are activated, number of LEDs to be activated, the colour of the LEDs, the brightness of the LEDs or other operational parameters. Further parameters may include combinations of periods of active and inactive lighting activity. In some embodiments the user can manually override the preconfigured parameters or can set parameters for a user defined test procedure. The parameters and operation mode selected by the user are confirmed at 905. At 910 an operation initiation signal is transmitted to headset 800. As discussed above, communications between the computing device 850 and headset 800 may be implemented over a wireless communication network, a wired network or any other suitable communication path.

Embodiments of the invention include a routine to ensure the device is correctly configured and positioned to receive clean EEG data. This involves having the subject have their eyes open for up to 30 seconds and then closed for up to 30 seconds whilst an initial recording verifies that an EEG alpha rhythm is being received. Once that has been ascertained the rest of the testing sequence is initiated by the software on the phone. If the EEG alpha rhythm is not received, steps are suggested to improve electrode contact, reposition headset etc or check equipment functioning correctly.

At 915 the operation initiation signal is received at the headset from the communicating device. The processor initiates the electrodes on the headset are activated at 920. A user may select to activate particular electrodes within the headset for a particular test. For example a specific number or group of electrodes.

In embodiments particular subsets of the electrodes can be activated for a particular test. In further embodiments on the invention an electrode initiation sequence is executed to confirm operation of activated electrodes.

After activation of electrodes processor 8040 initiates LED driver 8020. As discussed above, LED driver 8020 controls operation of LEDs 8010. LED driver 8020 initiates activation LED's in accordance with the user input requirements. As discussed above, LED driver controls activation of LEDs in accordance with the test requirements including activation of particular LEDs, length of stimulation periods, brightness of LEDs, colour of the LEDs, frequency at which LEDs are activated, variation in flashing frequency, intensity, wavelength, variation in wavelength, the order in which LEDs are activated and the sequencing for activation. A soothing component or sequence may be initiated pre-testing.

At 930 electrodes measure electrical potential during the test. The electrical potential measured by each electrode is stored at 935.

Measured electrical potential values may be stored locally in memory 8050 or maybe transmitted back to the computer device for storage at memory 8130. In some embodiments measurements are stored locally and remotely. In some embodiments results are transmitted to cloud based storage and/or processors.

On completion of the test, LEDs and electrodes are deactivated.

Results Analysis

After completion of a test the electrical potential measurements from the electrodes are analysed. Preferred embodiments of the invention compare outputs of the electrical potential amplitude measured by the electrodes. Preferably diagnostic algorithms are used to detect symptoms associated with mild Traumatic Brain Injury. Parameters compared include the time delay, amplitude, frequency associated with the measured electrical potentials and other parameters associated with the electrical potential waveform. Systems detect the delay or discrepancies in stimulated period lengths to detected period lengths or rest periods.

In preferred embodiments of the invention the electrical potential measured by the reference electrodes is subtracted from the electrical potential measured by the electrodes in the Occipital lobes to remove any background signals. The system looks for an alteration of visual evoked potential waveform amplitude or latency when compared to a previous baseline or to a normative database.

In preferred embodiments of the invention the measured results are compared with predefined results, for example baseline or normative models. These predefined results may have been taken previously, for example for a sports team the results may have been taken in the pre-season to establish a baseline reading for the player. In further embodiments of the invention a predefined range is set outside the predefined results beyond which functional disorder of the brain is diagnosed.

In some embodiments results processing is performed entirely on-board the headset according to individual settings using memory 8050 and processor 8040. Further embodiments perform analysis using a combination of on-board and internet (cloud based) analysis applied to the patient results and across a population of patients, or categories of patients.

In preferred embodiments the diagnostic algorithms account for the individual's historic measurements for detection in order to compare the current performance of the patient's brain with its previous or normal performance. Some diagnostic algorithms account for the historic measurements across user groups and populations. Analytics performed locally on the headset, on the computing device or in the cloud and the diagnostic algorithms may be used to predict or infer the influence of fatigue, time of day, exercise regimes, diseases, medications, a history of concussion, a history of trauma or of other neurological disorders.

Embodiments of the invention compare the results and trigger an alert if the waveform of the potential measured by the electrodes is outside the predefined range. The alert may be an audio alarm from the computer device or a visual alert from the computer device. Further embodiments of the invention include alternative alert mechanisms, for example vibrator devices, or networked messaging systems for example email.

In some embodiments, to better quantify the strength of the SSVEP response, an algorithm is used which utilises the mean amplitude, standard deviation and peak amplitude of the frequency response. By taking into account standard deviation, larger inconsistencies in frequency response are accounted for when rating the response. This rating is unitless.

The steps to this algorithm are as follows:

Step 1: Apply 3rd order Butterworth bandpass filter, with corner frequencies 5-35 Hz to data stream(s). This will normally be data from electrode positions O1, O2 and Oz.

Step 2: Perform Fast Fourier Transform (FFT) with Hanning windowing on data from step 1.

Step 3: Combine data from step 2 into one dataset.

Step 4: Calculate from data from step 3, the following:

(a) Average amplitude (p) between 5 Hz to 35 Hz. In other words, sum all values from the corresponding FFT bins between 5 Hz and 35 Hz, then divide by the number of bins.

(b) Standard deviation (a) between 5 Hz to 35 Hz.

(c) Peak amplitude between (v) 14.5 Hz and 15.5 Hz. In other words, the highest amplitude recorded between 14.5 Hz and 15.5 Hz.

Step 5: The rating is expressed as: Rating=$(v-\mu)/\sigma$

Figure 10:
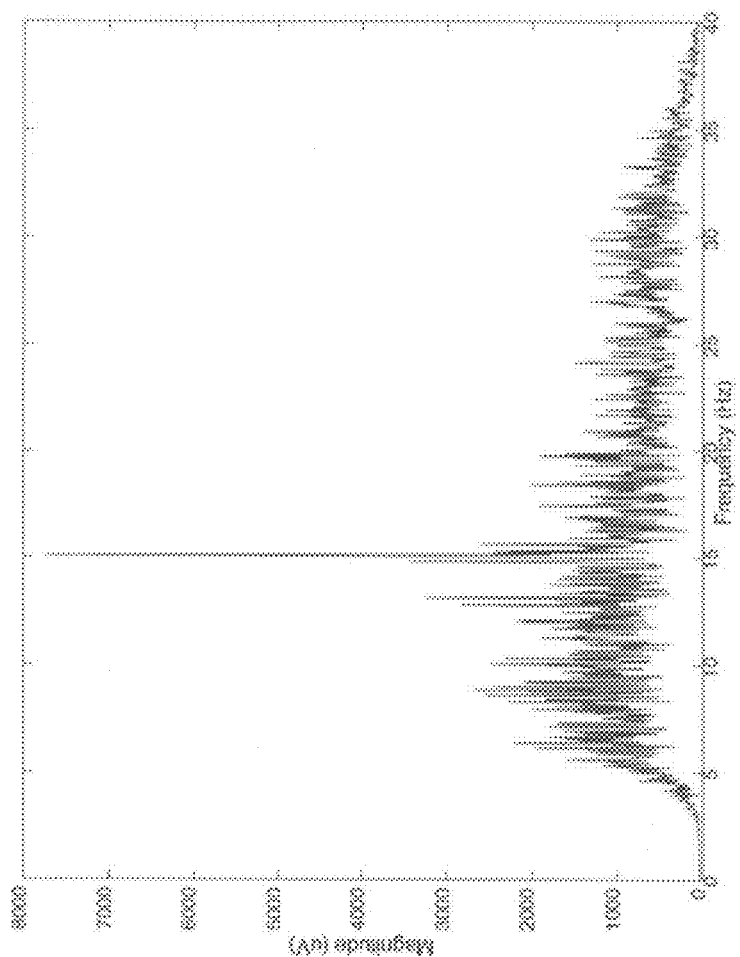
FIG. 10 is a graph showing measured response to a visual stimulus.
Figure 11:
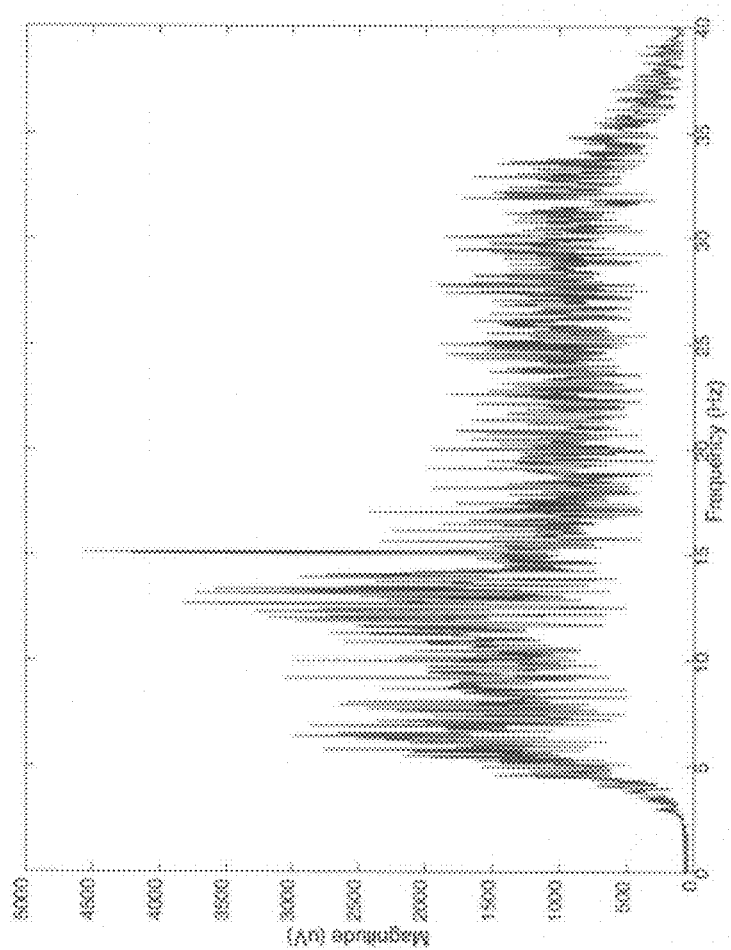
FIG. 11 is a graph showing measured response to a visual stimulus.

FIGS. 10 and 11 show example graphical representations of a Fourier transformation of signals measured by electrodes 1210. The graphs show the frequency response of the electrodes. Typically, in healthy individuals, a high and distinct fundamental frequency will be observed with the frequency matching the frequency of the visual stimulus. FIG. 10 shows a response measured by electrodes in a healthy individual. A high and distinct response is measured at around 15 Hz. FIG. 11 shows a response measured by electrodes in an individual suffering a functional disorder of the brain. The graph of FIG. 11 shows a lower response which is less distinct.

The frequency response for injured players typically yields a less definitive fundamental frequency, or in more severe cases even lack the fundamental frequency.

Figure 22:
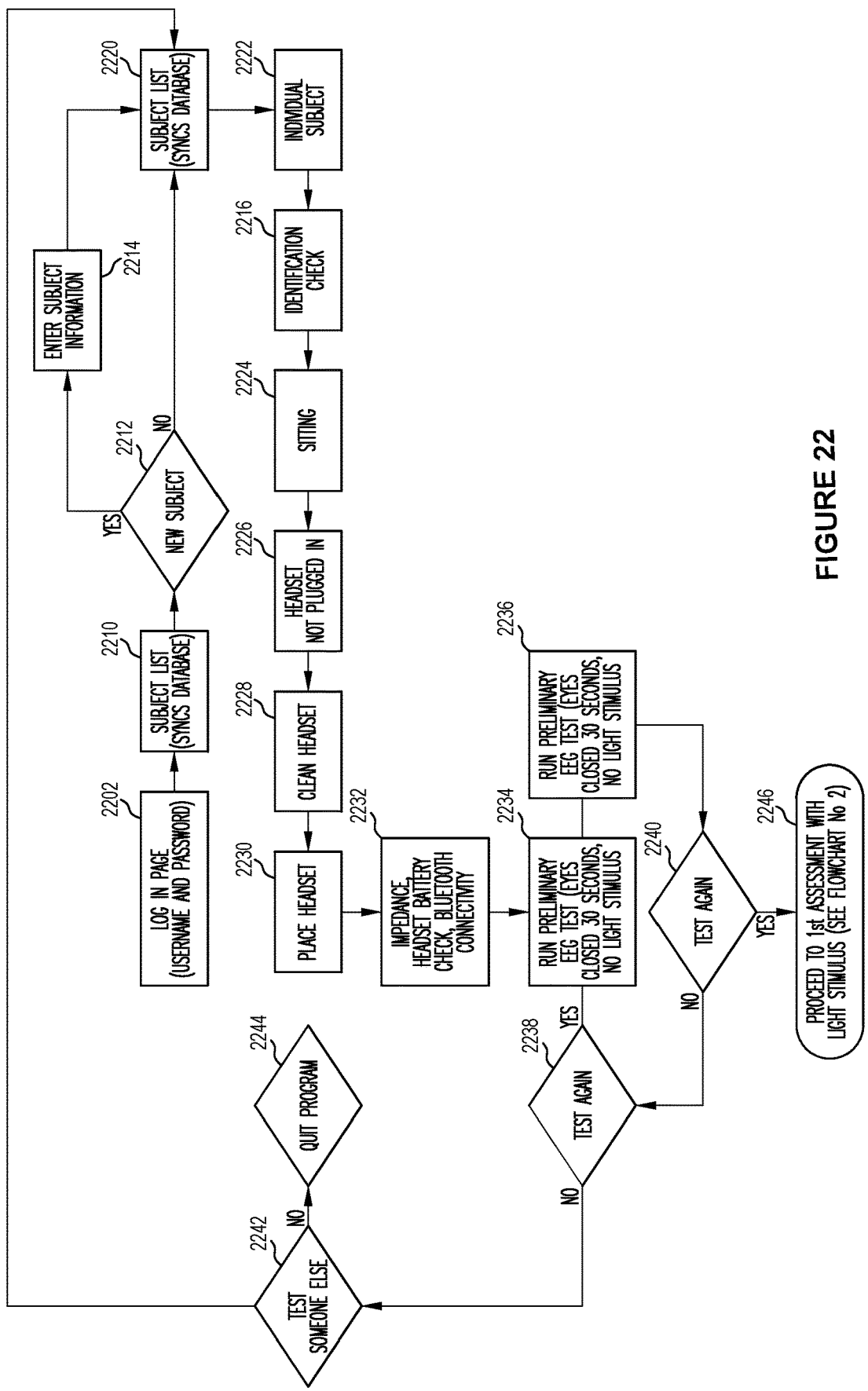
FIGS. 22 and 23 are flow charts showing the operation of an embodiment.
Figure 23:
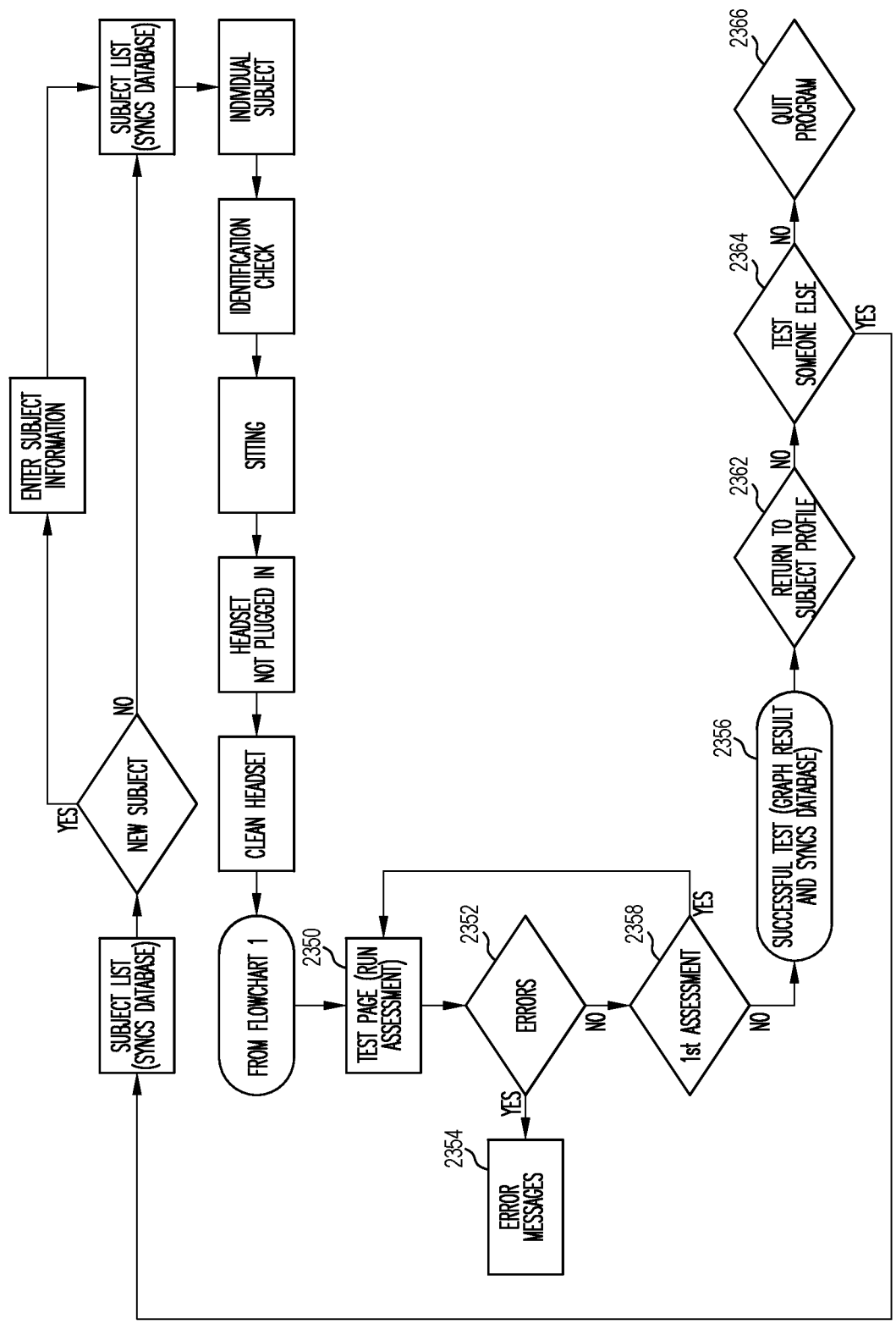

A further detailed description of the set up and use procedure is now described with reference to FIGS. 22 and 23. The procedure of FIG. 22 is described in relation to a clinician having a number of patients executing the test on behalf of a patient. In the example of FIG. 22 the headset is controlled via an application running on a computer or smart phone connected to headset across a communications network.

On establishing an active communications signal between the computer and the headset and activating the necessary software on the computer the clinician opens the login page at 2202. If the clinician is not yet registered, he may register at this stage. The clinician's lists of patients are presented at 2210. In the case that the patient is not yet registered under the clinician at 2212, patient information is included into the system at 2214. Any further authentication requirements, for example photo ID or other further authentication requirements may be met at this stage. Patient list 2210, 2220 may be stored locally and may also be synchronised with cloud storage database. Further identification checks may be performed at 2216.

In order to prepare the system and the patient for testing the patient is seated at 2224. If the headset is plugged into a charging module this must be removed at 2226. The headset may be prepared for use by cleaning and by the application of saline solution to the electrodes to ensure the electrodes are wet to the touch at 2228. This decreases impedance of the EEG signals.

At 2230 the headset is positioned on the head of the patient. Headsets may be positioned differently depending on the particular configuration of that headset but, typically, the headband is positioned above the ears and adjusted to snuggly fit the patient. The headset is positioned symmetrically on the head.

Test procedures may be run at 2232 including impedance check, battery check may be tested for required power output and temperature of the device may also be checked to ensure it conforms to the necessary temperature limits and connection test over Bluetooth or other wireless communication network. If not conforming, an error message may be displayed.

At 2234 the preliminary EEG test based on alpha wave is conducted. As described above, this involves having the patient have their eyes open for up to 30 second and providing no light stimulus. At 2236 preliminary EEG test is run with eyes closed for up to 30 seconds with no light stimulus. An initial recording verifies that an EEG alpha rhythm is being received. If no EEG signal is detected at 2240 preliminary EEG test is run again at 2238 until an EEG signal is detected at 2236. After a successful test at 2240 the patient proceeds to the first test. Patients are instructed to keep their eyes open for the duration of the full test. The test is run at 2350 (FIG. 23). If errors are detected at 2252 the test may be re-run. Further tests may be required at this stage for verification of results. If no further tests are required the clinician can conduct the first assessment at 2358 and upon a successful test, the results are saved and return to patient profile 2362 or progress with further tests on other patients.

Embodiments of the invention provide a system and method for detecting a functional disorder of the brain by measuring evoked potential from a visual response. Embodiments of the present invention provide an advantage that the performance of the nerves within the brain can be assessed quickly, consistently and in a non-subjective manner. This is particularly significant in a sporting environment in which a diagnosis is required to be made quickly. The electronic nature of the device also enables predefined results and previous player results to be stored and compared at the time of the test in order to aid with the diagnosis.

As discussed above embodiments of the system are connected to communications networks to enable local or remote analysis and diagnosis of results. All results (including existing standard observations and tests) may be incorporated by the on-board, on-phone, or online systems (or any combination of these) by algorithms, including machine learning methods, for concussion diagnosis or longer term concussion research through internet ("cloud") analytics and detection of emergent relationships that are not currently established.

Embodiments of the invention remove the need for subjective assessments. Instead, the tests conduct scientific measurements to assess the performance of the nerves within the brain.

In the embodiments described above the headset is illustrated as a single unit. In further embodiments of the invention the visor providing the visual stimulus could be provided in a separate unit from the electrode array. In further embodiments the housing need not include all electrical components of the device but the LED driver, memory, processor, wireless modules and power supplies may be positioned within other components of the system.

In the embodiments described above with reference to the figures the visor is in the shape of a pair of sports glasses. Further embodiments include alternative shaped visors. Other head wear suitable for presenting a visual stimulation to the eyes of a user, for example, a helmet or screen is included in the embodiments. Further embodiments include various headsets, goggles and virtual reality visors.

In a further embodiment of the invention the system can be implemented and controlled via a smartphone, for example under the control of an application on the smartphone. The headset can be substituted by a smartphone providing a visual stimulus and electrode positioned over the visual cortex in communication with the smartphone either by being plugged directly into the phone in a wired connection (even through the microphone/line in port) or mediated by a wireless or Bluetooth coupled component. The smartphone may be used within a virtual reality type holder. In such embodiments the application controls the visual output and receives and analyses the electric potentials received from the occipital sensors.

The smartphone can communicate guidelines and instructions to the patient and test information as well as generate visual stimulation patterns.

In further embodiment of the invention, the test routine may also audit the user's vestibular sense and sensitivity through an onboard test that utilizes, for example, a smartphone compass, accelerometer and gyroscope sensors. The screen utilize augmented or virtual reality conditions to invoke challenges and controls for vestibular testing.

Embodiments of the invention may be used to "profile" a potential patient, for instance in pre-season testing of sports players who are likely to suffer mild traumatic brain injury, in order to determine the modalities to which those patients are most sensitive in testing. This will create a "thumbprint" or "passport" for that individual allowing the most refined and sensitive testing following an injury and during recovery.

It may also be compared to normative data and responses to elucidate an individual's susceptibility to change following trauma, or their "concussion threshold".

After a collision or other event which could potentially result in a head injury, the EEG test is run on the individual. The same test is run after the collision as the profile test and the results are compared to make an assessment of whether the individual has a disorder of the brain.

Example 2

The aim of this study was to evaluate the utility of a portable electrophysiology platform to record measurable SSVEPs from healthy individuals.
Participants All participants were screened for a history of epilepsy, seizures and existing or previous brain injuries and conditions. Any positive findings excluded the participant from the study.
Equipment Two main components of the system were identified: the visual stimulus generation component, and the EEG recorder. A computer was used to capture the data from the EEG recorder, and perform signal analysis on the data.

The visual stimulus was delivered in two separate setups: a portable smartphone setup, and another utilising a traditional LCD computer monitor. For the portable setup, a Sony Xperia Z1 Compact smartphone (Sony Corporation, Minato, Tokyo, Japan) housed in a Google Cardboard (Google Inc., Googleplex, Mountain View, California, U.S.A.) was used. A Dell U2415 LCD monitor (Dell Technologies, One Dell Way, Round Rock, Texas, U.S.A.) was used as the traditional LCD monitor.

The EEG recorder was an Emotiv EPOC+ 14-channel portable wireless headset (Emotiv Inc., San Francisco, California, U.S.A.). This headset has 14 saline-moistened electrodes and 2 more for a common-mode-sense/driven-right-leg feedback system. Only the O1 and O2 electrodes along with ground electrodes were used for recording the output from the occipital region relating to visual signals. The Emotiv headset includes software that runs under a Windows operating system which captures data from the headset and records it into a European Data Format (EDF) standard file format. The headset sampling rate was set to 128 Hz.

Processing of data was performed on MATLAB (MathWorks, Inc., Natick, Massachusetts, U.S.A.) with the use of the Signal Processing Toolbox.

The stimuli were generated on MATLAB in the form of a MP4 movie sequence file. Two sets of stimuli were created: one incorporating a simple flicker stimulus, the other with a checkered pattern stimulus. Both stimuli incorporated a fixation target in the form of a centrally placed number.

As video compression can introduce compression artifacts, the movie file was inspected in Adobe Premiere CC frame-by-frame for any frame artifacts (i.e. a black frame becoming grey). It was found to be free of such compression artifacts.
Environment The experiments were performed in a quiet room. The response quality when using the LCD display was significantly affected by environmental light, and therefore all lights to the room were turned off during testing. Environmental conditions related to external noise, and intensity and directionality of ambient light sources were kept consistent throughout all testing.
Experimental Setup The experiment was divided into 2 separate stages. The first stage evaluated each parameter associated with SSVEPs and determined optimal parameters. The second stage validated the optimal parameters on a larger population.

The EPOC+ headset was paired via Bluetooth to the computer and fitted to each participant. The appropriate impedance was verified by the included software. Between each test there was one minute of rest. All tests were repeated once.

For tests requiring the portable SSVEP, the smartphone was powered on and the stimulus was displayed. The smartphone was then housed in the Google Cardboard and provided to the user. The participant held the system in their hands, then held the unit to their face to observe the stimulus upon test commencement. The participant was sitting throughout the test.

Figure 12:
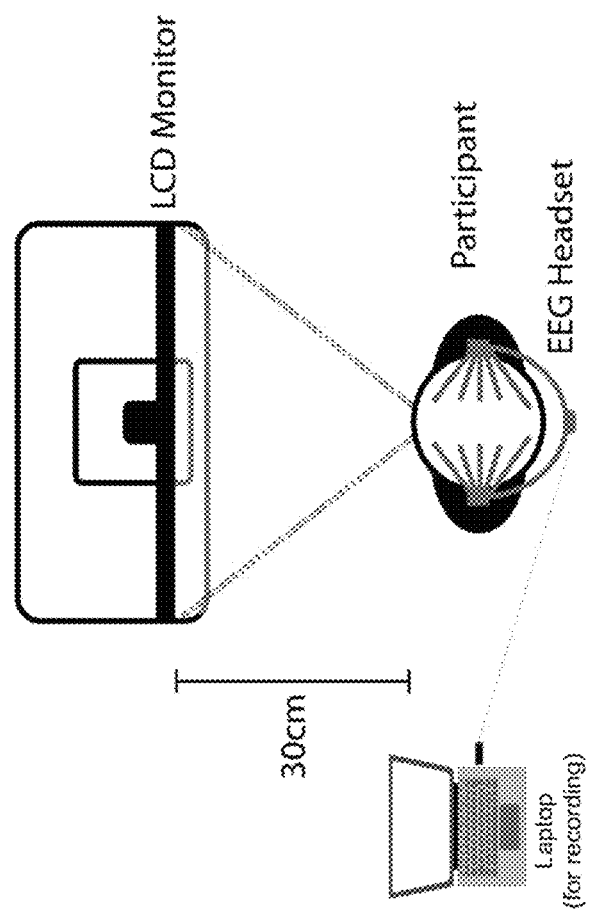
FIG. 12 is a diagram of setup for LCD monitor stimulus.

For tests requiring the LCD computer monitor, the stimulus was displayed on the monitor. Users were required to sit 30 cm from the monitor as seen in FIG. 12.
Experiment I The aim of Experiment I was to evaluate the optimal parameters for a portable SSVEP system, as well as comparing the portable system (the smartphone/Cardboard combination) against LCD monitors conventionally used for SSVEP applications. 4 parameters were evaluated: the delivery platform, type of stimulus image, stimulus frequency and epoch length.
Delivery Platform A 30-second viewing of the stimulus was performed by the 4 subjects twice for each platform. A 15 Hz flash stimulus with a fixation target was used.

Participants were initially evaluated on the computer LCD display positioned 30 cm from each participant. Once the stimulus commenced, all participants were instructed to concentrate on the fixation target. The recording was started remotely on the computer connected via Bluetooth to the EPOC+.

Participants were next evaluated utilising the portable system. After confirming they could see the stimulus, the recording was remotely started from the connected computer.

Figure 13:
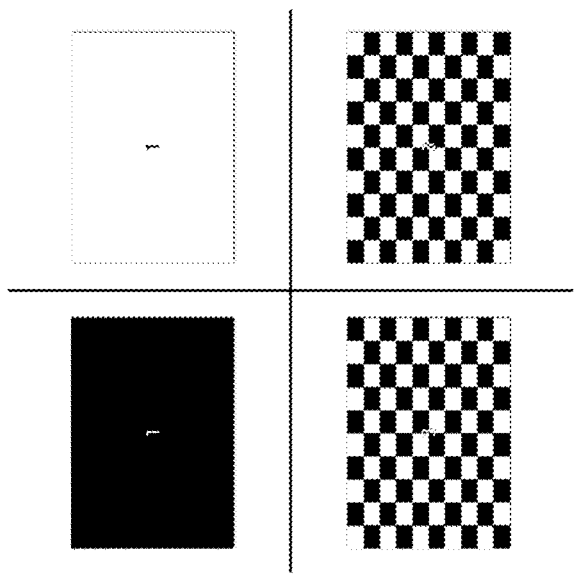
FIG. 13 shows stimulus images used. Top row is flash stimulus; bottom is pattern stimulus. Stimuli alternated between images.

Stimulus Image 4 subjects were evaluated with a 30-second 15 Hz visual stimulus of both a pattern reversal and a flash pattern on an LCD monitor. Each stimulus image was evaluated twice (FIG. 13). The order of the stimulus images was randomised for all participants. All participants were instructed to concentrate on the fixation, then the recording was started remotely.

Stimulus Frequency

Figure 14:
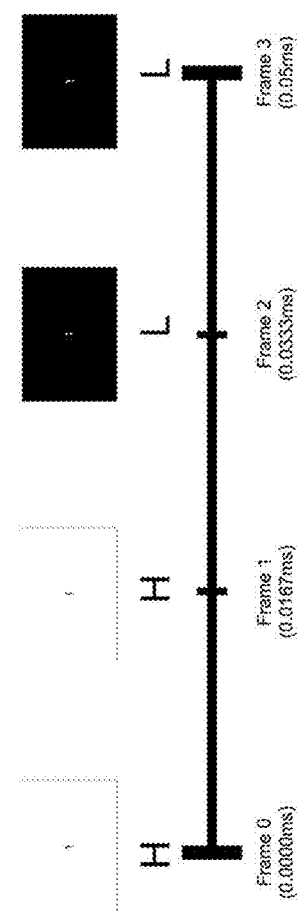
FIG. 14: Timing pattern for 15 Hz frequency. Note the H and L pattern, using either the 'white' or 'black' stimulus.

Both patterns with a fixation target were displayed at 12, 15, 20 and 30 Hz, each for 30 seconds. The portable stimulus platform was used, and all 4 participants were evaluated twice for each frequency. The frequencies and their associated frame output are seen in Table 3 and FIG. 14.

TABLE 3

Frequencies and Rendering Pattern for 60 Hz Table 3:
Frequencies and Rendering Pattern for 60 Hz Displays

| Frequency | Period | Pattern |
|---|---|---|
| 6 | 166.67 | HHHHHLLLLL |
| 6.66 | 150 | HHHHHLLLL |
| 7.5 | 133.33 | HHHHLLLL |
| 8.57 | 116.67 | HHHHLLL |
| 10 | 100 | HHHLLL |
| 12 | 83.33 | HHHLL |
| 15 | 66.67 | HHLL |
| 20 | 50.00 | HHL |
| 30 | 33.33 | HL |

Epoch Length

To evaluate all epoch lengths at once, all 4 participants were evaluated for 45 seconds with the portable stimulus platform, viewing a stimulus at 15 Hz of the flash-reversal pattern along with a fixation target. These epochs were cropped into 5, 10, 15 and 30-second segments for analysis.

Experiment II

Figure 15:
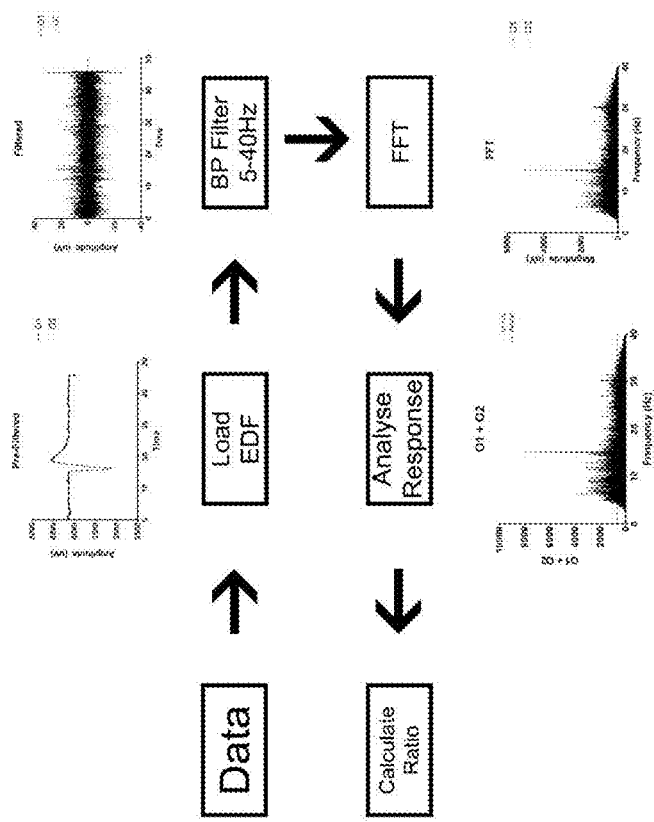
FIG. 15 shows a flow chart of data analysis.

After evaluating the results from Experiment I, it was determined that the portable stimulus platform performed similarly to an LCD monitor, and that a 15 Hz flash stimulus with a fixation point and a length of 30 seconds was optimal. All subjects were evaluated twice with these parameters. A flow chart is seen in FIG. 15.

Data Analysis

All data from the Emotiv EPOC+ was captured with the Emotiv Xavier Testbench software into a European Data Format (EDF) file.

Each EDF file was imported into MATLAB for preparation and analysis. The O1 and O2 channels were selected for analysis. No downsampling of signals was required as the EPOC+ headset has already downsampled the data from 2048 Hz to 128 Hz.

Signal Filtering

Both the O1 and O2 channels were filtered with a 3rd-order Butterworth bandpass filter with 5-40 Hz window. An infinite-impulse response-type (IIR) filter was chosen for its small delay and efficiency. When choosing coefficients for the IIR filter, instability testing was performed using the MATLAB Signal Processing Toolbox (specifically the isstable function) to prevent uncontrolled filter outputs from occurring. For the filter design, a Butterworth IIR filter was chosen due to its lack of ripple in the passband.

The lower cut-off frequency was chosen due to high levels of noise present in the lower frequency caused by skin impedance. The higher cut-off frequency was chosen to eliminate mains noise (occurring at 50 Hz) and preventing aliasing. The Nyquist frequency was 64 Hz (as the sampling rate was 128 Hz), resulting in all frequencies beyond 64 Hz being aliased. In addition, as there was 50 Hz interference caused by surrounding electrical appliances. A cut-off of 40 Hz filters the aliasing without resorting to a steeper and less stable filter.

The initial 5 seconds was cropped as user testing found that there was significant eye blinking whilst habituating to the stimulus as testing began, which then ceased.

Signal Transformation

A Fast Fourier Transform (FFT) was performed on the filtered O1 and O2 channels. Only frequencies between 0-40 Hz were plotted, as frequencies beyond the bounds were filtered.

The O1 and O2 channels were combined together into one output.

Quantification of Response

A simple algorithm was proposed to quantify the frequency response. The average background spectral activity (or noise) from 0-40 Hz was acquired, and then a ratio between the peak 15 Hz magnitude and the background noise was recorded.

The equation can be expressed as:

$$\text{Ratio\_response} = (\text{Amplitude\_15 Hz})/(\text{Amplitude\_average}).$$

Statistical Analysis

All statistical analysis was performed on GraphPad Prism 7.02 (Graph Pad Software, Inc., 5755 Oberlin Drive, #110, San Diego, CA 92121, U.S.A.). D'Agostino & Pearson normality tests were performed on the data to determine the distribution pattern.

Results

Experiment I 4 healthy adults (3 males, 1 female, Mage=21.5, SDage=1.708) participated in Experiment I. All 4 subjects had 20/20 vision, and successfully completed all sections of Experiment I.

Delivery Platform

The mean Ratio Response of the LCD monitor was 6.415±0.627. Use of the portable platform yielded similar response ratios to the LCD monitor, with a mean Ratio Response of 6.199±0.501.

TABLE 4

Response for Different Delivery Platforms

| Subject | Traditional LCD | Portable |
|---|---|---|
| 1 | 7.327 | 6.912 |
| 2 | 5.911 | 5.752 |
| 3 | 6.274 | 5.995 |
| 4 | 6.147 | 6.138 |
| Mean | 6.415 | 6.199 |
| SD | 0.6265 | 0.5012 |

Stimulus Image

Both the pattern reversal and flash reversal images had similar responses, with a mean Ratio Response of 6.142±0.353 and 6.199±0.443 respectively.

TABLE 5

Response Ratios for Different Stimulus Images

| Subject | Flash Rev. | Pattern Rev. |
|---|---|---|
| 1 | 6.721 | 6.634 |
| 2 | 5.625 | 5.807 |
| 3 | 6.015 | 6.120 |
| 4 | 5.865 | 6.006 |
| Mean | 6.057 | 6.142 |
| SD | 0.4712 | 0.3527 |

Stimulus Frequency

Table 6 summarises the results of differing stimulus frequencies. A stimulus frequency of 15 Hz yielded the strongest response (Mean=6.319±0.416), while 12 Hz performed slightly poorer while still yielding a response (Mean12 Hz=4.754±0.4342). 20 Hz and 30 Hz frequencies generated no visible response. The presence of harmonic frequencies was noted for the 12 Hz and 15 Hz stimulus frequencies in the form of visible peaks at 24 Hz and 30 Hz respectively.

TABLE 6

Response Ratios of Different Frequencies

| Subject | 12 Hz | 15 Hz | 20 Hz | 30 Hz |
|---|---|---|---|---|
| 1 | 5.167 | 5.912 | 3.742 | 2.768 |
| 2 | 4.657 | 6.015 | 2.953 | 2.635 |
| 3 | 4.977 | 6.841 | 3.164 | 2.597 |
| 4 | 4.216 | 6.506 | 2.817 | 3.016 |
| Mean | 4.754 | 6.319 | 3.169 | 2.754 |
| SD | 0.416 | 0.4342 | 0.4078 | 0.1894 |

Epoch Length

Table 7 summarises the results concerning epoch length. A 45 second epoch had a mean Ratio Response of 7.144±0.513, while a 5 second epoch had a mean Ratio Response of 2.793±0.597, demonstrating the effect of epoch length on the response.

TABLE 7

Response Ratios of Different Epoch Lengths

| Subject | 5 s | 10 s | 15 s | 30 s | 45 s |
|---|---|---|---|---|---|
| 1 | 3.125 | 4.263 | 4.621 | 7.285 | 7.617 |
| 2 | 2.838 | 3.136 | 3.941 | 7.332 | 7.519 |
| 3 | 1.939 | 3.467 | 4.804 | 6.373 | 6.537 |
| 4 | 3.269 | 2.941 | 5.546 | 6.476 | 6.903 |
| Mean | 2.793 | 3.452 | 4.728 | 6.865 | 7.144 |
| SD | 0.5967 | 0.5828 | 0.6597 | 0.5137 | 0.5134 |

Experiment II

Experiment II evaluated 20 healthy adults (13 males, 7 females, Mage=36.47, SDage=18.54). All 20 participants had 20/20 vision, and successfully completed Experiment II.

The SSVEP parameters used for Experiment II were determined from Experiment I.

Using the portable stimulus system, a flash-reversal image flickering at 15 Hz recorded for 30 seconds was used. With these parameters, the mean Ratio Response was 5.551±1.164.

A D'Agostino & Pearson normality test was performed and had a P-value of 0.9019, meaning the data were consistent with a Gaussian distribution.

Discussion

In this study we have been able to show that an EEG can reliably detect a 15 Hz SSVEP in normal subjects from a stimulus generated on a portable smartphone system with the same reliability as a standard LCD monitor.

The proposed system serves as a proof of concept for a dedicated portable diagnostic system. The results demonstrate that a reliable and consistent response can be expected from a healthy population. This may be utilised in the context of sports-related concussion, where an abnormal response may indicate the presence of concussion.

Concussion is currently diagnosed with a clinical diagnosis aided with a symptom checklist, neurocognitive and balance tests. This approach is subjective and prone to observer bias. Conventional imaging modalities, such as computed tomography (CT) and magnetic resonance imaging (MRI) can only be used to rule out severe brain injuries, but cannot detect concussion.

Conclusion

We have shown that it is possible to reliably detect a steady-state visual-evoked potential response in healthy controls using a portable platform. We found that a 15 Hz stimulus, with central fixation target and a test time of 30 seconds had the most robust, reliable and reproducible results. This testing set-up was achievable with a smartphone, Cardboard headset and a currently available wireless EEG recording headset.

Example 3

In a further study, the purpose was to evaluate the utility of a portable SSVEP platform in identifying concussion in rugby union players and to identify when they are recovered. A prospective cohort observational study was undertaken over a season of rugby union training and match activities. A total of 65 (20.9±2.3 yr.) players were enrolled in the study. Player screening was undertaken to identify any possible contraindications to participating in the study, and for history of concussion. Tests were performed on a weekly schedule during the rugby club's training time.

Figure 16B:
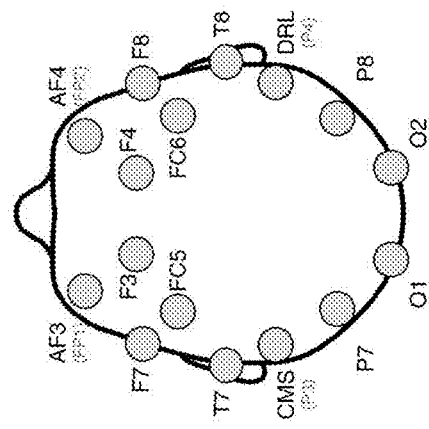
FIG. 16B shows electrode positions.
Figure 16A:
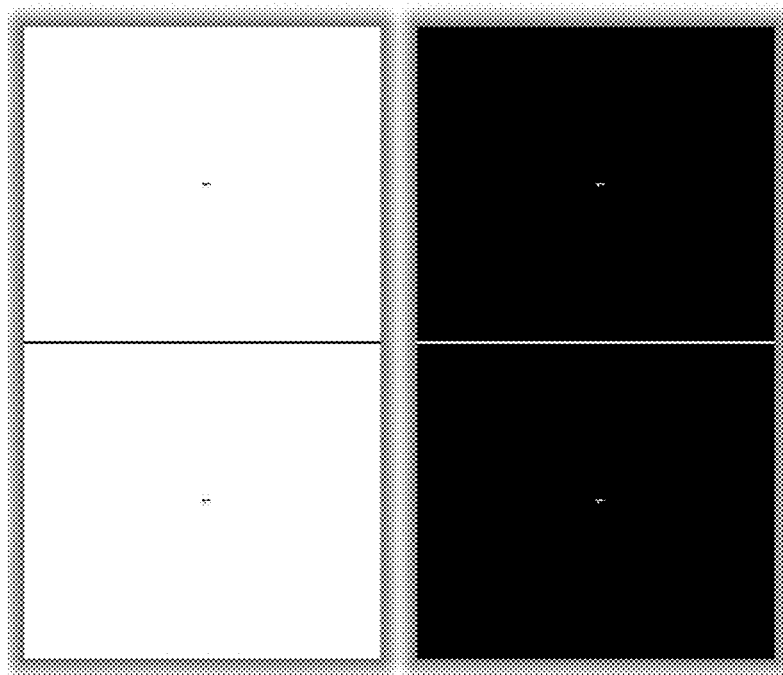
FIG. 16A shows an example of the visual stimulus.

The visual stimulus utilised for this study (See FIG. 16A) were displayed on a Sony Xperia Z1 Compact smartphone in a MP4 video file. The smartphone was placed in a Google Cardboard headset and the participant held this to their head covering both eyes. The MP4 video comprised a sequence of black and white screens alternating at 15 Hz. A number was placed in the middle of the screen (occupying less than 2% of the screen with a visual angle of 1.5°) to allow participants to focus centrally to maximise participant concentration and field of view covered by the stimulus. This number changed at 5 second intervals to improve user concentration.

The EEG recordings were undertaken with a wireless, 14-channel EEG headset (Emotiv EPOC+; Emotiv Systems, Inc. San Francisco, CA. http://www.emotiv.com). The electrodes were arranged according to the International 10-20 system (see FIG. 16B). The O1 and O2 electrodes were used as the main recording electrodes and the P3 and P4 electrodes were utilised as a reference point (P3) and for feedback cancellation (P4) respectively. Data was sampled at 128 Hz and wirelessly transferred to a laptop computer (Sony Vaio Pro 11 laptop (Sony Corporation, Minato, Tokyo, Japan)) via the Emotiv Xavier TestBench v3.1.21 software as a European Data Format (EDF) file.

FIG. 16 shows A: An example of the visual stimulus used as the stimulus. The stimulus alternated between the top and bottom picture at a rate of 15 times per second. There is a fiducial line in the middle used to align the screen with the Google Cardboard headset. The number changed at 5 second intervals and participants were instructed to focus on the number for a total of 30 seconds. NB: The shadow does not exist on the actual stimulus but is utilised here to make the visual stimulus clearer to view. (B): Emotiv EPOC+ electrode positions. Only electrodes P3, P4, O1 and O2 were utilised: P3 and P4 were utilised as a common-mode subtraction/driven-right-leg reference and ground, and O1 and O2 were the analysed electrodes.

Prior to the competition season, all enrolled players underwent the screening assessment. Once enrolled, all participants underwent the EEG test twice (for test-retest reliability purposes). Throughout the competition season, at training sessions typically two days after a competition game, participants were fitted with the EPOC+ headset and their SSVEP acquired. To ensure an adequate connection between the headset and the participant's head, the Emotiv TestBench software's contact quality indicator was checked before the test was undertaken. If the quality indicator indicated a poor connection, the headset was removed, and the electrode pads relubricated with saline solution. The headset housing the smartphone was provided to the subject; they were instructed to hold it up to their eyes and stare at the number at the centre of the screen to minimise eye movements for 30 seconds whilst trying not to blink. The test was then repeated for a total of 2 consecutive recordings. Following a head injury, or a medically diagnosed concussion, the test was repeated twice to assess for any changes in the SSVEP. The test was also repeated periodically during the season for assess for test-retest reliability. To address potential bias, the administrator of the test did not know the condition of the player until after the data was processed.

The captured EDF file data was imported into MATLAB 2015b (MathWorks, Inc.,

Natick, Massachusetts; http:www.mathworks.com). A band-pass Butterworth filter with corner frequencies at 5 Hz and 40 Hz was applied to minimise lower-frequency noise, DC voltage offset and mains power hum. A Fast Fourier Transformation (FFT) was then applied to generate a frequency-magnitude graph of the combined O1 and O2 channels. The average magnitude (MagAvg) between 5-40 Hz and 15 Hz (Mag15) was calculated to establish the magnitude ratio (MagRatio) between the Mag15 and the MagAvg. The MagRatio was utilised for comparison purposes across the different groups. As each participant had 2 test results, the higher MagRatio results were utilised.

Statistical analysis was performed utilising IBM SPSS software (International Business Machines Corporation, New York, U.S.A.) and the graphs were plotted in GraphPad Prism 7 (GraphPad Software Inc., CA, U.S.A.). A Shapiro-Wilk normality test determined the data to be normally distributed (control W=0.97; p=0.2902, concussed W=0.96; p=0.4154, recovered W=0.90; p=0.5987). Paired and unpaired single-tailed t-tests were performed between the 3 groups (control-concussed, control-recovered, and concussed-recovered) and a Bonferroni correction was utilised for all post-hoc analyses. Test-retest reliability was estimated utilising the intra-class correlation coefficient (ICC), with 95% confidence intervals (CI), to examine agreement between baseline and repeated testing throughout the season. Cohen's effect size (d) was utilised to calculate practically meaningful differences between controls, concussed and recovered. Effect sizes of <0.19, 0.20-0.60, 0.61-1.20 and >1.20 were considered trivial, small, moderate, and large, respectively [25]. All summarised data are expressed as means (with 95% CI) and median (25th to 75th interquartile range). Statistical significance level was set at $\alpha=0.05$.

Results

Notable changes were observed in the stimulus response strength (MagRatio) in the identified concussed participants when compared to the control subjects (2.00 [95% CI: 1.83 to 2.16] vs. 5.01 [4.78 to 5.24]; p<0.0001) (see Table 1). 8 of the participants who were re-evaluated after recovery had an increased MagRatio compared to the concussed SSVEP (see Table 2).

TABLE 8

VEP MagRatio values of total participants and participants that recorded a concussion by mean with 95% Confidence Intervals and Median with interquartile [25th to 75th] ranges and the differences between control, concussed and recovered participants. Matched Participants only includes participants who were in all 3 study groups over the season.

| Group | $Mag_{Ratio}$ score Mean (95% CI) | $Mag_{Ratio}$ score Median [IQR] | vs. Control diff (p-value); d= | vs. Concussed diff (p-value); d= | vs. Recovered diff (p-value); d= |
|---|---|---|---|---|---|
| Total participants | | | | | |
| Control | 5.01 (4.78-5.24) | 4.80 [4.07-5.68] | — | -2.80 (<0.0001); 4.03 | +0.02 (0.0117); 0.40 |
| Concussed | 2.00 (1.83-2.16) | 2.00 [1.40-2.32] | +2.80 (<0.0001); 4.03 | — | +2.82 (<0.0001); 5.25 |
| Recovered | 4.44 (3.90-4.98) | 4.82 [4.13-5.18] | -0.02 (0.0117); 0.40 | -2.82 (<0.0001); 5.25 | — |
| Matched participants | | | | | |
| Control | 4.45 (3.85-5.06) | 4.54 [3.79-5.10] | — | -2.25 (0.0001); 4.20 | -0.12 (0.0495); 0.17 |
| Concussed | 2.20 (2.01-2.38) | 2.20 [2.04-2.38] | 2.25 (0.0001); 4.20 | — | -2.47 (0.0002); 3.60 |
| Recovered | 4.67 (4.20-5.13) | 4.82 [4.13-5.18] | 0.12 (0.0495); 0.17 | -2.47 (0.0002); 3.60 | — |

CI: Confidence Interval;

IQR = Interquartile [25th to 75th] range;

diff = differences between $Mag_{Ratio}$;

d = Cohen's d effect size

TABLE 9

Player who recorded a concussion response to the visual stimulus (MagRatio) at control (baseline), immediately after concussion, and subsequent recovery by actual results with differences between the different assessments.

| | Mag$_{Ratio}$ | | | Differences identified | | |
|---|---|---|---|---|---|---|
| | | | | Cont vs. Conc; | Conc vs. Rec; | Rec vs. Cont; |
| Player | Control | Concussed | Recovered | p-value | p-value | p-value |
| AH | 4.52 | 2.33 | 4.24 | 2.19; 0.1970 | −1.92; 0.1801 | −0.28; 0.0203 |
| JH | 3.32 | 2.05 | 3.10 | 1.27; 0.1481 | −1.05; 0.1280 | −0.22; 0.0217 |
| JJ2 | 4.55 | 2.31 | 4.68 | 2.24; 0.2008 | −2.37; 0.2078 | 0.13; 0.0088 |
| PC | 3.99 | 2.03 | 3.77 | 1.95; 0.1996 | −1.74; 0.1850 | −0.22; 0.0177 |
| TJ | 5.09 | 2.09 | 5.17 | 3.00; 0.2522 | −3.09; 0.2559 | 0.09; 0.0053 |
| TS | 5.35 | 1.85 | 5.21 | 3.50; 0.2882 | −3.36; 0.2830 | −0.14; 0.0083 |
| TG | 3.72 | 2.51 | 3.48 | 1.21; 0.1220 | −0.98; 0.1027 | −0.23; 0.0205 |
| LS | 5.10 | 2.40 | 4.96 | 2.70; 0.2197 | −2.55; 0.2125 | −0.15; 0.0092 |
| Total | 4.45 | 2.20 | 4.33 | 2.26; 0.0001 | −2.13; 0.0002 | 0.13; 0.0495 |

The control ratio was acquired before a concussion; the concussed ratio up to 72 hours after a concussion; the recovered ratio after being clinically declared to return-to-play; Cont = Control; Conc = Concussed; Rec = Recovered

TABLE 10

Test-retest reliability of the SSVEP and EEG findings for players who have undergone multiple testing throughout the season.

| Group | N= | ICC (95% CI) | Med. Time (IQR) | Mean Time |
|---|---|---|---|---|
| Control | 22 | 0.91 (0.79-0.96) | 36 (26-39) | 31.91 ± 11.22 |
| Concussed | 3 | 0.29 (−0.91-0.97) | 7 (7-7) | 7.00 ± 0.00 |
| Recovered | 5 | 0.96 (0.74-0.99) | 16 (13-23) | 17.60 ± 6.23 |

Control test-retest were performed on players periodically over the season who had not recorded a concussion; Concussed test-retest were performed after 3-7 days post-concussion, and not yet clinically declared to return-to-play; Recovered test-retest were performed periodically on players who were formally concussed but have since been medically declared recovered. Med. Time: median time between testings. Mean time: mean time between testings.

A reduction in the alpha rhythms and increase in theta rhythms (8-12 Hz) of concussed participants was also observed. Upon recovery, the alpha and theta rhythms returned to baseline conditions (see FIG. 17).

Figure 17:
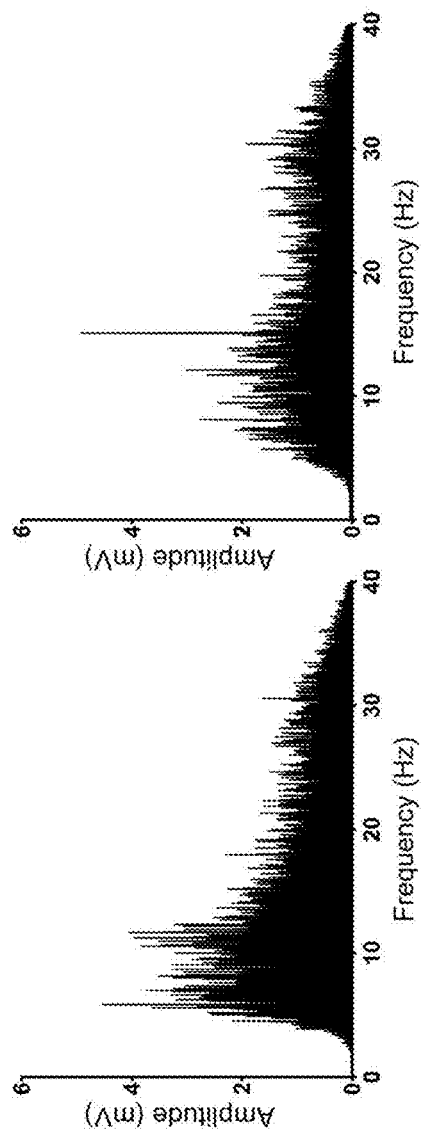
FIG. 17 shows Fourier transformations of the frequency spectrum.
Figure 18:
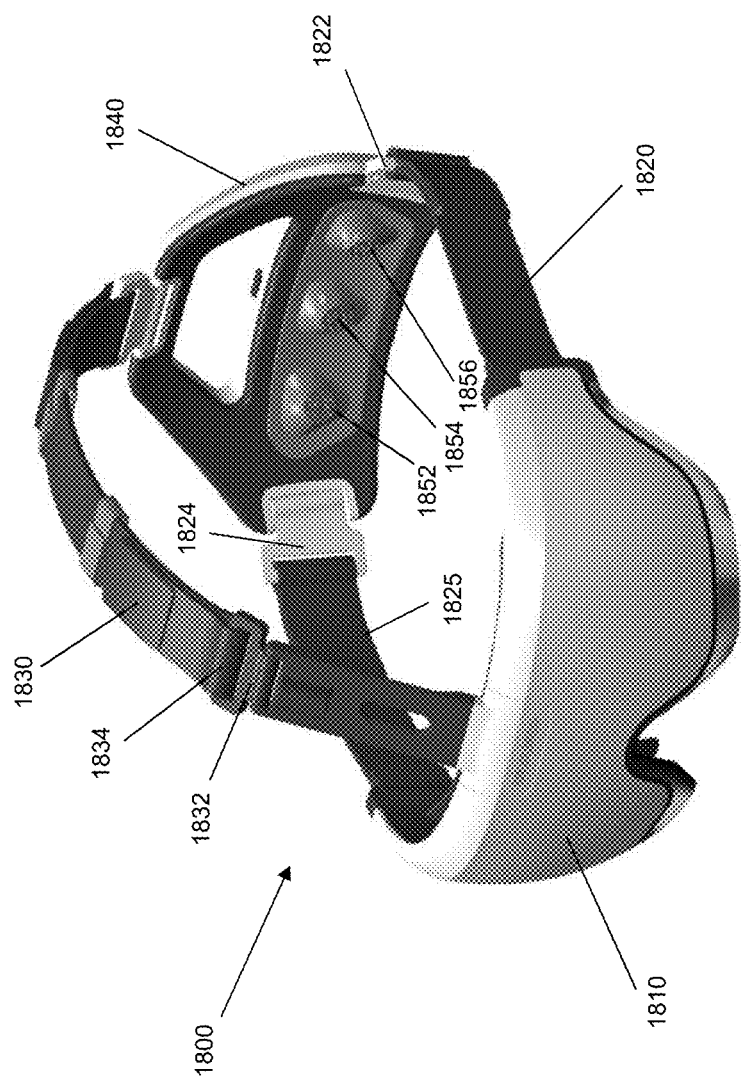
FIG. 18 is a perspective view of a second embodiment of a head mountable device.
Figure 19:
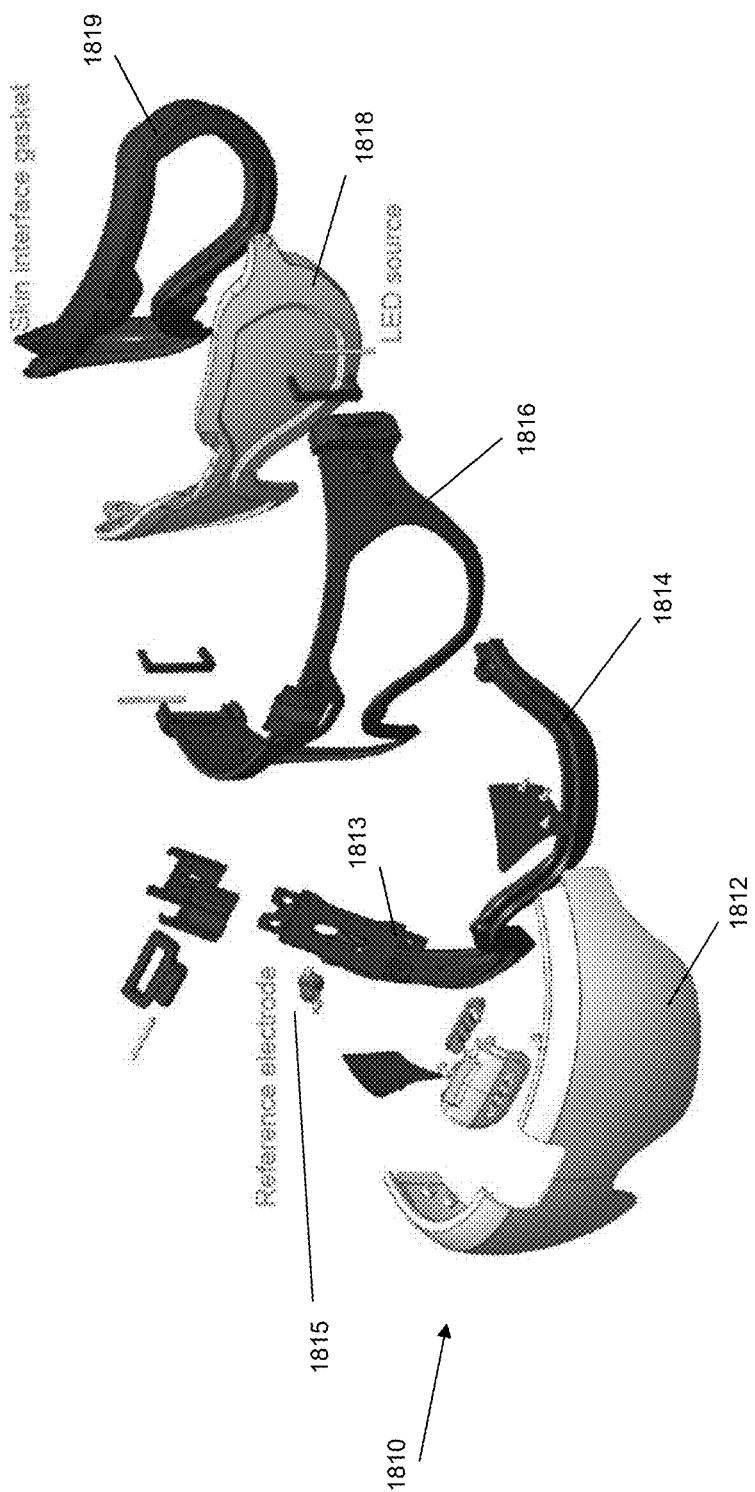
FIG. 19 is an exploded view of a visor in the second embodiment.

FIG. 17 shows Fourier transformations of the frequency spectrum (SSVEP) comparisons of player JJ2 when identified with a medically diagnosed concussed (left) and when medically cleared to return-to-play (right) Note the reduction in alpha rhythm and increase in theta rhythm on the left figure. Also note the presence of a large peak at 15 Hz on the right figure, demonstrating response to the 15 Hz visual stimulus.

Some control participants also demonstrated a smaller 30 Hz harmonic frequency in addition to their 15 Hz fundamental frequency (see FIG. 17 right). This phenomenon was only observed in 16 control participants, but was not observed in any of the concussed participants.

The study demonstrated the recovery to pre-concussion SSVEP parameters following medically assessed diagnosis of concussion and clinical recovery.

The high test-retest reliability for control and recovered groups highlights the consistency of the measurement, even when the repeated testing was conducted several weeks apart.

There are several advantages of using SSVEP compared with conventional VEP such as: (1) lack of synchronicity between EEG recorder and visual stimulus (simplifying equipment requirements), (2) relative resistance to noise artefacts; and (3) improved resilience to variable contact impedance. These advantages make SSVEP a better system for use in non-clinical environments such as on the sideline of sports grounds and in general practitioner surgeries.

The use of imaging modalities such as magnetic resonance imaging (MRI) and computed tomography (CT) are primarily for anatomic imaging, and therefore provide information about structural problems. As concussion is not a macroscopic structural injury, these imaging modalities do not aid in the diagnosis, but can be utilised to rule out any structural injuries. However, VEP testing assesses for function rather than structural integrity and reflects the physiology of the brain. Thus, the absence of the response to the 15 Hz stimulus found in this study may represent an objective assessment criterion for concussion. The use of VEP's such as the SSVEP utilised in this study has the potential to be a supplemental aid for the assessment of, and identification by a medical practitioner in the clinical diagnosis of a concussion.

The background noise was variable even among the same individuals tested again immediately after their first test. Possible reasons may be due to: (1) poor impedance control (as the system does not feedback the actual impedance values); and (2) variable visual focus during tests due to fatigue or distractions. Testing alongside other EEG equipment may provide a deeper insight into whether these variances are naturally occurring, or a shortcoming of the current equipment. Applying a refractive blur to the stimulus may also identify if pupil, convergence or accommodation changes affect the responses identified.

The reduction in the alpha rhythm and increase in theta rhythm have been previously reported and this phenomenon may not be exclusively attributed to sports-related concussion. Reduced alpha rhythm has been previously associated with drowsiness and sleepiness; increased theta rhythm has been associated with cognitive and emotional processes, particularly stress. Also observed was the presence of a harmonic frequency in the form of a secondary response at 30 Hz in some participants. Previous non-clinical studies have identified this harmonic frequency, and have leveraged it to improve classification accuracy for brain-computer interface solutions. However, its diagnostic utility especially in concussion injuries has yet to be determined. A possible solution would be to further stratify study groups to identify if the presence of the harmonic frequency is a random effect or if it is specific under certain conditions.

In most participants, the second test response was stronger than the first. This was hypothesised to be due to familiarisation with the process and lessened blinking.

Electroencephalography and SSVEP offers new potential in the assessment of concussion, by non-invasively and objectively measuring brain function. This study undertook to identify if there were differences in concussed participants utilising SSVEP via a portable device. The study also assessed return towards the same individual's previous (baseline) response following a concussive injury.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A head mountable device for detecting a functional disorder of a brain in a patient, comprising:
    an opaque visor unit for positioning over eyes of the patient, wherein the visor unit includes: an arrangement of a plurality of LEDs positioned on an inside surface of said visor unit to which, during use, the eyes of the patient are exposed;
    a sensor housing including:
        three electroencephalogram (EEG) recording electrodes for measuring electrical potentials generated by the brain of the patient,
        an LED driver configured to control each of the plurality of LEDs independently to display a visual stimulus,
        a processor for controlling activation of the three EEG recording electrodes and the LED driver, and
        a battery for powering the LEDs and the processor;
    a headband coupling the sensor housing to the visor unit, wherein the LED driver is coupled to each of the plurality of LEDs by electrical connections from the sensor housing to the visor unit
    a first reference electrode configured to provide a reference point against which electrical potential signal data is measured by each of the three EEG recording electrodes; and
    a second reference electrode configured to provide a feedback cancellation signal;
    the device being configured to be mountable on a head of the patient such that when mounted on the head of the patient the plurality of LEDs are positioned before the eyes of the patient and the three EEG recording electrodes are positioned adjacent to an occipital lobe of the patient to receive signals from O1, O2, and Oz of the occipital lobe of the patient, respectively.

2. The head mountable device according to claim 1, wherein said visor unit further comprises:
    a bridge suitable for positioning said visor unit on a nose of the patient, said arrangement of said plurality of LEDs being positioned symmetrically on both sides of said bridge on said inside surface of said visor unit.

3. The head mountable device according to claim 1, wherein said LED driver is adapted to activate said plurality of LEDs in a predefined illumination sequence, wherein said predefined illumination sequence includes at least one of simultaneous illumination of the plurality of LEDs, sequential illumination of the plurality of LEDs, and selective activation of the plurality of LEDs.

4. The head mountable device according to claim 1, wherein said LED driver is adapted to activate said plurality of LEDs in a predefined flashing pattern.

5. The head mountable device according to claim 1, wherein the visual stimulus is a light pulse, and wherein the plurality of LEDs are controlled to generate visual stimulus light pulses at a frequency of between 5 Hz to 60 Hz.

6. The head mountable device according to claim 5, wherein the visual stimulus light pulses at a frequency of 15 Hz.

7. The head mountable device according to claim 1, wherein the visual stimulus is white light.

8. The head mountable device according to claim 1, wherein the three EEG recording electrodes are configured to detect electrical signals from the occipital lobe of the patient in response to the visual stimulus when the device is mounted on the head of the patient.

9. The head mountable device according to claim 1, further comprising:
    a memory, the memory being configured to store predetermined electrical potential data,
    wherein the processor is configured to:
        receive electric potential signal data from the three EEG recording electrodes with reference to said first reference electrode; and
        compare said received electric potential signal data with said stored predetermined electric potential data to detect a functional disorder of the brain,
    wherein the predetermined electric potential data are at least one of:
        amplitude of an electric signal;
        frequency of the electric signal; or
        latency of the electric signal.

10. The head mountable device according to claim 1, wherein the functional disorder of the brain is selected from the group consisting of: concussion, neurological impairment, dementia, and multiple sclerosis.

11. The head mountable device according to claim 1, further comprising a receiver, the receiver configured to receive activation signals for the plurality of LEDs, the plurality of LEDs being configured to display the visual stimulus on receipt of an activation signal, wherein the receiver is one of:
    (i) a radio receiver configured to receive activation signals from a computing device across a wireless communications network; or
    (ii) a radio receiver configured to receive activation signals from a computing device across a wireless communications network.

12. The head mountable device according to claim 1, the sensor housing further comprising a sensor plate, wherein said sensor plate includes said first reference electrode and said second reference electrode positioned substantially horizontally above said three EEG recording electrodes, said sensor plate being configured to be positioned at the rear of the head of the patient when in use such that the three EEG recording electrodes are configured to be positioned adjacent to the occipital lobe of the patient.

13. The head mountable device of claim 1, wherein the sensor housing further includes:
   a pre-amplifier to amplify said measured electrical potential signal data.

14. The head mountable device of claim 1, wherein the headband is adjustable.

15. The head mountable device of claim 1, further comprising:
   a skin interface gasket coupled to said visor unit and configured to contact a face of the patient when the device is mounted on the head of the patient.

16. The head mountable device of claim 1,
   wherein said sensor housing further includes a support configured to hold the device in position on the head of the patient, and
   further wherein at least one of said opaque visor unit and support is made from a polymer.

17. A system for detecting a functional disorder of a brain in a patient, the system comprising:
   a head mountable device according to claim 1, wherein the head mountable device further comprises:
   a receiver configured for receiving electric potential signal data from at least one of the three EEG recording electrodes; and
   a wired or wireless transmitter configured for transmitting said received electric potential signal data and said reference electrical potential; and the system further comprising:
   a computing device, said computing device including:
   a wired or wireless receiver configured for receiving said transmitted electric potential signal data;
   a computing device memory configured for storing predefined results; and
   a computing device processor configured to compare said electric potential signal data with said stored predefined results to diagnose a condition of the patient.

18. A method for detecting a functional disorder of a brain in a patient, the method comprising the steps of:
   using the head mountable device according to claim 1 to provide the visual stimulus to the patient;
   measuring an electrical response of the brain to the visual stimulus using at least one of the three EEG recording electrodes positioned adjacent to the occipital lobe of the patient; and,
   comparing the electrical response of the brain to predefined electrical data to detect the functional disorder of the brain.

19. A method for detecting a functional disorder of a brain in a patient using the system of claim 17, the method comprising the steps of:
   using the head mountable device to provide the visual stimulus to the patient;
   measuring an electrical response of the brain to the visual stimulus using at least one of the three EEG recording electrodes positioned adjacent to the occipital lobe of the patient;
   transmitting the measured electrical response to the computing device; and
   utilizing the computing device processor to compare the electrical response of the brain to predefined results to diagnose the functional disorder of the brain.

* * * * *